(12) United States Patent
Hudkins

(10) Patent No.: US 6,635,669 B2
(45) Date of Patent: *Oct. 21, 2003

(54) ISOMERIC FUSED PYRROLOCARBAZOLES AND ISOINDOLONES

(75) Inventor: Robert L. Hudkins, Chester Springs, PA (US)

(73) Assignee: Cephalon, Inc., West Chester, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/062,159

(22) Filed: Feb. 1, 2002

(65) Prior Publication Data

US 2002/0147341 A1 Oct. 10, 2002

Related U.S. Application Data

(62) Division of application No. 09/640,825, filed on Aug. 17, 2000.
(60) Provisional application No. 60/150,367, filed on Aug. 20, 1999.

(51) Int. Cl.$^7$ .................... A61K 31/403; A61K 31/407; C07D 401/02; C07D 401/05

(52) U.S. Cl. ............... 514/410; 514/338; 514/339; 548/416; 546/276.7

(58) Field of Search ............... 546/276.7; 514/338, 514/339, 410; 544/109; 548/126, 416

(56) References Cited

U.S. PATENT DOCUMENTS

| 5,475,110 A | * | 12/1995 | Hudkins et al. | ........... 536/17.4 |
| 5,705,511 A | * | 1/1998 | Hudkins et al. | ........... 514/338 |
| 5,808,060 A | * | 9/1998 | Hudkins et al. | ........... 540/577 |

* cited by examiner

Primary Examiner—Rita Desai
(74) Attorney, Agent, or Firm—Robert T. Hrubiec; Eric K. Voelk; Scott K. Larsen

(57) ABSTRACT

The present invention is directed to novel fused pyrrolocarbazoles and isoindolones, including pharmaceutical compositions, diagnostic kits, assay standards or reagents containing the same, and methods of using the same as therapeutics. The invention is also directed to intermediates and processes for making these novel compounds.

15 Claims, No Drawings

ISOMERIC FUSED PYRROLOCARBAZOLES AND ISOINDOLONES

This application is a divisional of U.S. Ser. No. 09/640825 filed filed Aug. 17, 2000 and claims priority to provisional application No. 60/150,367 filed Aug. 20, 1992.

FIELD OF THE INVENTION

The present invention relates generally to isomeric fused pyrrolocarbazoles and isoindolones, including pharmaceutical compositions, diagnostic kits, assay standards or reagents containing the same, and methods of using the same as therapeutics. The invention is also directed to intermediates and processes for making these novel compounds.

BACKGROUND OF THE INVENTION

The microbial-derived material referred to as "K-252a" is a unique compound which has gained significant attention over the past several years due to the variety of functional activities which it possesses. K-252a is an indolocarbazole alkaloid that was originally isolated from a Nocardiosis sp. culture (Kase, H et al. 39 J. Antibiotics 1059, 1986). K-252a is an inhibitor of several enzymes, including protein kinase C (PKC) which plays a central role in regulating cell functions, and trk tyrosine kinase. The reported functional activities of K-252a and its derivatives are numerous and diverse: tumor inhibition (See U.S. Pat. Nos. 4,877,776, 4,923,986, and 5,063,330; European Publication 238,011 in the name of Nomato); anti-insecticidal activity (See U.S. Pat. No. 4,735,939); inhibition of inflammation (See U.S. Pat. No. 4,816,450); treatment of diseases associated with neuronal cells (See U.S. Pat. Nos. 5,461,146; 5,621,100; 5,621,101; and WIPO Publication WO 94/02488, published Feb. 3, 1994 in the names of Cephalon, Inc. and Kyowa Hakko Kogyo Co., Ltd); and treatment of prostate disease (See U.S. Pat. Nos. 5,516,771; and 5,654,427). K-252a also has been reported to inhibit IL-2 production (See Grove, D. S. et al., Experimental Cell Research 193: 175–182, 1991).

The reported indolocarbazoles share several common attributes. In particular, each comprises three five member rings which all include a nitrogen moiety; staurosporine (derived from Streptomyces sp.) and K-252a each further comprise a sugar moiety linked via two N-glycosidic bonds. Both K-252a and staurosporine have been extensively studied with respect to their utility as therapeutic agents. The indolocarbazoles are generally lypophilic, which allows for their comparative ease in crossing biological membranes, and, unlike proteinaceous materials, they manifest a longer in vivo half-life.

Although K-252a is normally derived from culture media via a fermentation process, the total synthesis of the natural (+) isomer and the unnatural (−) isomer, in which the three chiral carbons of the sugar have the opposite configurations, has been achieved (See Wood et al., J. Am. Chem. Soc. 117:10413, 1995, and WIPO Publication WO 97/07081). However, this synthesis is not practical for commercial use.

In addition to the indolocarbazole alkaloids represented by K-252a and staurosporine, synthetic small organic molecules which are biologically active and known as fused pyrrolocarbazoles have been prepared (See U.S. Pat. Nos. 5,475,110; 5,591,855; 5,594,009; 5,705,511; and 5,616, 724).

Fused isoindolones which are non-indole-containing molecules that can be chemically synthesized de novo are also known (See U.S. Pat. No. 5,808,060 and WIPO Publication WO 97/21677). Certain bis-indolylmaleimide macrocyclic derivatives have also been reported (See for example U.S. Pat. Nos. 5,710,145; 5,672,618; 5,552,396 and 5,545,636). Sugar derivatives of indolopyrrolocarbazoles also have been reported (see WIPO Publication WO98/07433). There remains a need for novel pyrrolocarbazole and isoindolone derivatives that possess beneficial properties. This invention is directed to this, as well as other, important ends.

SUMMARY OF THE INVENTION

Accordingly, one object of the present invention is to provide novel compounds which are kinase inhibitors. Particularly, the compounds of the present invention are inhibitors of trk kinase, platelet derived growth factor receptor (PDGFR) kinase, vascular endothelial growth factor receptor (VEGFR) kinase, or NGF-stimulated trk phosphorylation. Another object of the invention is to provide novel compounds which enhance the trophic factor-induced activities of trophic factor responsive cells.

It is another object of the present invention to provide pharmaceutical compositions having activity toward trk kinase, platelet derived growth factor receptor (PDGFR) kinase, vascular endothelial growth factor receptor (VEGFR) kinase, NGF-stimulated trk phosphorylation, or tropic factor responsive cells wherein the composition comprises a pharmaceutically acceptable carrier and a therapeutically effective amount of at least one of the compounds of the present invention, or a pharmaceutically acceptable salt form thereof It is another object of the present invention to provide a novel method for treating or preventing disorders associated with the aberrant activity of trk kinase, platelet derived growth factor receptor PDGFR) kinase, vascular endothelial growth factor receptor (VEGFR) kinase, NGF-stimulated trk phosphorylation, or tropic factor responsive cells, wherein the method comprises administering to a host in need of such treatment or prevention a therapeutically effective amount of at least one of the compounds of the present invention.

It is another object of the present invention to provide a method for inhibiting trk kinase, platelet derived growth factor receptor (PDGFR) kinase, vascular endothelial growth factor receptor (VEGFR) kinase, NGF-stimulated trk phosphorylation, or enhancing tropic factor responsive cell activity, in a body fluid sample wherein the method comprises treating the body fluid sample with an effective amount of at least one of the compounds of the present invention.

It is another object of the present invention to provide a kit or container containing at least one of the compounds of the present invention in an amount effective for use as a diagnostic, standard or reagent.

These and other objects, which will become apparent during the following detailed description, have been achieved by the inventor's discovery that compounds of Formula I:

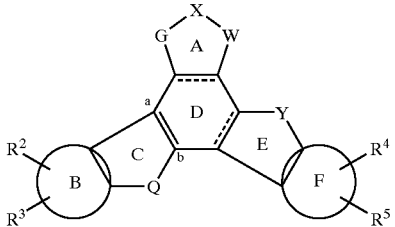

stereoisomeric forms, mixtures of stereoisomeric forms, or pharmaceutically acceptable salt forms thereof, wherein A, B, C, D, E, F, G, Q, X, W, Y, $R^2$, $R^3$, $R^4$, and $R^5$ are defined below, are effective kinase inhibitors.

DETAILED DESCRIPTION OF THE EMBODIMENTS

Thus, in a first embodiment, the present invention provides a novel compound of Formula I:

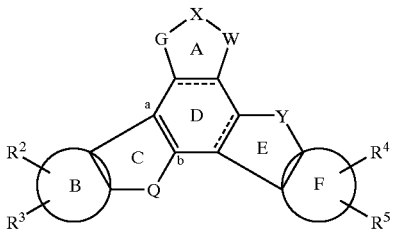

I or a stereoisomer or pharmaceutically acceptable salt form thereof, wherein:

ring D is selected from phenyl and cyclohexene with double bond a-b;

ring B and ring F, independently, and each together with the carbon atoms to which they are attached, are selected from:
  a) a 6-membered carbocyclic ring in which from 1 to 3 carbon atoms may be replaced by hetero atoms; and
  b) a 5-membered carbocyclic ring in which either
    1) one carbon atom may be replaced with an oxygen, nitrogen, or sulfur atom;
    2) two carbon atoms may be replaced with a sulfur and a nitrogen atom, an oxygen and a nitrogen atom, or two nitrogen atoms; or
    3) three carbon atoms may be replaced with three nitrogen atoms, one oxygen and two nitrogen atoms, or one sulfur and two nitrogen atoms;

G—X—W is selected from:
  a) —($A^1A^2$)C—N($R^1$)—C($B^1B^2$)—;
  b) —CH($R^{1A}$)—C(=O)—N($R^1$)—; and
  c) —N($R^1$)—C(=O)—CH($R^{1A}$)—;

$R^1$ is selected from:
  a) H, substituted or unsubstituted alkyl of 1 to 6 carbons, substituted or unsubstituted aryl, substituted or unsubstituted arylalkyl, substituted or unsubstituted heteroaryl, or substituted or unsubstituted heteroarylalkyl;
  b) —C(=O)$R^7$, where $R^7$ is selected from substituted or unsubstituted alkyl, substituted or unsubstituted aryl, substituted or unsubstituted carbocyclic group, and substituted or unsubstituted heterocyclyl groups;
  c) —$OR^8$, where $R^8$ is selected from H and alkyl having from 1 to 6 carbons;

d) —C(=O)$NHR^8$, —$NR^9R^{10}$, —$(CH_2)_pNR^9R^{10}$, —$(CH_2)_pOR^8$, —$O(CH_2)_pOR^8$ and —$O(CH_2)_pNR^9R^{10}$, where p is from 1 to 4; and where either
    1) $R^9$ and $R^{10}$ are each independently selected from H, unsubstituted alkyl of 1 to 6 carbons, and substituted alkyl; or
    2) $R^9$ and $R^{10}$ together form a linking group of the formula —$(CH_2)_2$—$X^1$—$(CH_2)_2$—, wherein $X^1$ is selected from —O—, —S—, and —$CH_2$—;

$R^{1A}$ is the same as $R^1$;

$R^2$, $R^3$, $R^4$ and $R^5$ are each independently selected from:
  a) H, aryl, carbocyclyl, heterocyclyl, —CN, $CF_3$, —$NO_2$, —OH, —$OR^7$, Br, I —$O(CH_2)_pNR^9R^{10}$, —OC(=O)$R^7$, —OC(=O)$NR^9R^{10}$, —$O(CH_2)_pOR^8$, F, Cl, —$CH_2OR^8$, —$NR^9R^{10}$, —$NR^8S(=O)_2R^7$, —$NR^8C(=O)R^7$, or —$NR^8C(=S)R^7$;
  b) —$CH_2OR^{11}$, where $R^{11}$ is the residue of an amino acid after the hydroxyl group of the carboxyl group is removed;
  c) —$NR^8C(=O)NR^9R^{10}$, —$NR^8C(=S)NR^9R^{10}$, —$CO_2R^{12}$, —C(=O)$R^{12}$, —C(=O)$NR^9R^{10}$, —C(=S)$NR^9R^{10}$, —CH=$NOR^{12}$, —CH=$NR^7$, —$(CH_2)_pNR^9R^{10}$, —$(CH_2)_pNHR^{11}$, or —CH=$NNR^{12}R^{12A}$; where
    $R^{12}$ is selected from H, alkyl of 1 to 6 carbons, —OH, alkoxy of 1 to 6 carbons, —OC(=O)$R^7$, —OC(=O)$NR^9R^{10}$, —OC(=S)$NR^9R^{10}$, —$O(CH_2)_pNR^9R^{10}$, —$O(CH_2)_pOR^8$, substituted or unsubstituted arylalkyl having from 6 to 10 carbons, substituted or unsubstituted heterocyclylalkyl, and a substituted or unsubstituted carbocyclic group;
    $R^{12A}$ is the same as $R^{12}$;
  d) —$S(O)_yR^{12}$, —$(CH_2)_pS(O)_yR^7$, —$CH_2S(O)_yR^{11}$ where y is 0, 1 or 2;
  e) alkyl of 1 to 8 carbons, alkenyl of 2 to 8 carbons, and alkynyl of 2 to 8 carbons, wherein:
    1) each alkyl, alkenyl, or alkynyl group is unsubstituted; or
    2) each alkyl, alkenyl or alkynyl group is substituted with 1 to 3 groups selected from aryl of 6 to 10 carbons, heterocyclyl, arylalkoxy, heterocycloalkoxy, hydroxylalkoxy, alkyloxyalkoxy, hydroxyalkylthio, alkoxy-alkylthio, F, Cl, Br, I, —CN, —$NO_2$, —OH, —$OR^7$, —$X^2$ $(CH_2)_pC(=O)NR^9R^{10}$, —$X^2(CH_2)_pC(=S)$ $NR^9R^{10}$, —$X^2(CH_2)_pOC(=O)NR^9R^{10}$, —$X^2$ $(CH_2)_pCO_2R^7$, —$X^2(CH_2)_pS(O)_yR^7$, —$X^2(CH_2)_p$ $NR^8C(=O)NR^9R^{10}$, —OC(=O)$R^7$, —OC(=O) $NHR^{12}$, O-tetrahydropyranyl, —$NR^9R^{10}$, —$NR^8CO_2R^7$, —$NR^8C(=O)NR^9R^{10}$, —$NR^8C$ (=S)$NR^9R^{10}$, —NHC(=NH)$NH_2$, —$NR^8C$ (=O)$R^7$, —$NR^8C(=S)R^7$, —$NR^8S(=O)_2R^7$, —$S(O)_yR^7$, —$CO_2R^{12}$, —C(=O)$NR^9R^{10}$, —C(=S)$NR^9R^{10}$, —C(=O)$R^{12}$, —$CH_2OR^8$, —CH=$NNR^{12}R^{12A}$, —CH=$NOR^{12}$, —CH=$NR^7$, —CH=NNHCH(N=NH)$NH_2$, —$S(=O)_2NR^{12}R^{12A}$, —P(=O)$(OR^8)_2$, —$OR^{11}$, and a monosaccharide of 5 to 7 carbons where each hydroxyl group of the monosaccharide is independently either unsubstituted or is replaced by H, alkyl of 1 to 4 carbons, alkylcarbonyloxy of 2 to 5 carbons, or alkoxy of 1 to 4 carbons;

$X^2$ is O, S, or $NR^8$;

Q is selected from —$NR^6$, —O—, and —S—;

$R^6$ is selected from H, —$SO_2R^7$, —$CO_2R^7$, —C(=O)$R^7$, —C(=O)$NR^9R^{10}$, alkyl of 1–8 carbons, alkenyl of 2–8 carbons, and alkynyl of 2–8 carbons; and either 1) each alkyl, alkenyl, or alkynyl group is unsubstituted; or
2) each alkyl, alkenyl, or alkynyl group independently is substituted, as defined for $R^2$, $R^3$, $R^4$, and $R^5$ in e) above;

Y is selected from:
a) an unsubstituted alkylene of 1–3 carbons;
b) an alkylene of 1–3 carbons substituted with $R^{13}$, where $R^{13}$ is selected from $R^{12}$, thioalkyl of 1–4 carbons, halogen, alkyl of 1–8 carbons, alkenyl of 2–8 carbons, and alkynyl of 2–8 carbons, where
  i) each alkyl of 1–8 carbons, alkenyl of 2–8 carbons, and alkynyl of 2–8 carbons is unsubstituted; or
  ii) each alkyl of 1–8 carbons, alkenyl of 2–8 carbons, and alkynyl of 2–8 carbons, independently, is substituted, as defined for $R^2$, $R^3$, $R^4$, and $R^5$ in e) above; and
c) a functional group selected from —CH=CH—, —CH(OH)—CH(OH)—, —O—, —S—, —S(=O)—, —S(=O)$_2$—, —C($R^6$)$_2$—, —C=C($R^{13}$)$_2$—, —C(=O)—, —C(=NO$R^{12}$)—, —C(O$R^{12}$)$R^{12}$—, —C(=O)CH($R^6$)—, —CHR($R^6$)C(=O)—, —C(=NO$R^{12}$)CH($R^6$)—, —CH$R^8$C(=NO$R^{12}$)—, —C(=O)N($R^8$)—, —N($R^8$)C(=O)—, —CH$_2$Z—, —ZCH$_2$—, and —CH$_2$ZCH$_2$—, where Z is selected from —C($R^{12}$)—, —O—, —S—, —CO$_2R^{12}$, —C(=NO$R^{12}$)—, and —N($R^{12}$)—;

$A^1$ and $A^2$ are selected from H, H; H, O$R^{12}$; H, —S$R^{12}$; H, —N($R^{12}$)$_2$; and a group where $A^1$ and $A^2$ together form a moiety selected from =O, =S, and =N$R^{12}$; and, $B^1$ and $B^2$ are selected from H, H; H, —O$R^{12}$; H, —S$R^{12}$; H, —N($R^{12}$)$_2$; and a group where $B^1$ and $B^2$ together form a moiety selected from =O, =S, and =N$R^{12}$; with the proviso that at least one of the pairs $A^1$ and $A^2$, or $B^1$ and $B^2$, form =O.

In another embodiment, the present invention provides a novel compound of Formula XXII:

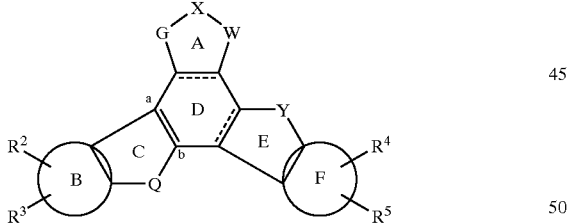

XXII or a stereoisomer or pharmaceutically acceptable salt form thereof, wherein:

ring D is selected from phenyl and cyclohexene with double bond a-b;

ring B and ring F, independently, and each together with the carbon atoms to which they are attached, are selected from:
a) a 6-membered carbocyclic ring in which from 1 to 3 carbon atoms may be replaced by hetero atoms; and
b) a 5-membered carbocyclic ring in which either
  1) one carbon atom may be replaced with an oxygen, nitrogen, or sulfur atom;
  2) two carbon atoms may be replaced with a sulfur and a nitrogen atom, an oxygen and a nitrogen atom, or two carbon atoms; or
  3) three carbon atoms may be replaced with three nitrogen atoms, one oxygen and two nitrogen atoms, or one sulfur and two nitrogen atoms;

G—X—W is selected from:
a) —($A^1A^2$)C—N($R^1$)—C($B^1B^2$)—;
b) —CH($R^{1A}$)—C(=O)—N($R^1$)—; and
c) —N($R^1$)—C(=O)—CH($R^{1A}$)—;

$R^1$ is selected from:
a) H, substituted or unsubstituted alkyl of 1 to 6 carbons, substituted or unsubstituted aryl, substituted or unsubstituted arylalkyl, substituted or unsubstituted heteroaryl, or substituted or unsubstituted heteroarylalkyl;
b) —C(=O)$R^7$, where $R^7$ is selected from substituted or unsubstituted alkyl, substituted or unsubstituted aryl, substituted or unsubstituted aralkyl, substituted or unsubstituted carbocyclic group, and substituted or unsubstituted heterocyclyl groups;
c) —O$R^8$, where $R^8$ is selected from H and alkyl having from 1 to 6 carbons;
d) —C(=O)N$R^8$, —N$R^9R^{10}$, —(CH$_2$)$_p$N$R^9R^{10}$, —(CH$_2$)$_p$O$R^8$, —O(CH$_2$)$_p$O$R^8$ and —O(CH$_2$)$_p$N$R^9R^{10}$, where p is from 1 to 4; and where either
  1) $R^9$ and $R^{10}$ are each independently selected from H, unsubstituted alkyl of 1 to 6 carbons, and substituted alkyl, substituted or unsubstituted aryl, substituted or unsubstituted heteroaryl; or
  2) $R^9$ and $R^{10}$ together form a linking group of the formula —(CH$_2$)$_2$—$X^1$—(CH$_2$)$_2$—, wherein $X^1$ is selected from —O—, —S—, and —CH$_2$—;

$R^{1A}$ is the same as $R^1$;

$R^2$, $R^3$, $R^4$ and $R^5$ are each independently selected from:
a) H, aryl, carbocyclyl, heterocyclyl, —CN, CF$_3$, —NO$_2$, —OH, —O$R^7$, Br, I, —O(CH$_2$)$_p$N$R^9R^{10}$, —OC(=O)$R^7$, —OC(=O)N$R^9R^{10}$, —O(CH$_2$)$_p$O$R^8$, F, Cl, —CH$_2$O$R^8$, —N$R^9R^{10}$, —N$R^8$S(=O)$R^7$, —N$R^8$C(=O)$R^7$, or —N$R^8$C(=S)$R^7$;
b) —CH$_2$O$R^{11}$, where $R^{11}$ is the residue of an amino acid after the hydroxyl group of the carboxyl group is removed;
c) —N$R^8$C(=O)N$R^9R^{10}$, —N$R^8$C(=S)N$R^9R^{10}$, —CO$_2R^{12}$, —C(=O)$R^{12}$, —C(=O)N$R^9R^{10}$, —C(=S)N$R^9R^{10}$, —CH=NO$R^{12}$, —CH=N$R^7$, —(CH$_2$)$_p$N$R^9R^{10}$, —(CH$_2$)$_p$NH$R^{11}$, or CH=NN$R^{12}R^{12A}$; where
$R^{12}$ is selected from H, alkyl of 1 to 6 carbons, —OH, alkoxy of 1 to 6 carbons, —OC(=O)$R^7$, —OC(=O)N$R^9R^{10}$, —OC(=S)N$R^9R^{10}$, —O(CH$_2$)$_p$N$R^9R^{10}$, —O(CH$_2$)$_p$O$R^8$, substituted or unsubstituted arylalkyl having from 6 to 10 carbons, substituted or unsubstituted heterocyclylalkyl, and a substituted or unsubstituted carbocyclic group;
$R^{12A}$ is the same as $R^{12}$;
d) —S(O)$_yR^{12}$, —(CH$_2$)$_pS(O)_yR^7$, —CH$_2$S(O)$_yR^{11}$ where y is 0, 1 or 2;
e) alkyl of 1 to 8 carbons, alkenyl of 2 to 8 carbons, and alkynyl of 2 to 8 carbons, wherein:
  1) each alkyl, alkenyl, or alkynyl group is unsubstituted; or
  2) each alkyl, alkenyl or alkynyl group is substituted with 1 to 3 groups selected from aryl of 6 to 10 carbons, heterocyclyl, arylalkoxy, heterocycloalkoxy, hydroxylalkoxy, alkyloxyalkoxy, hydroxyalkylthio, alkoxy-alkylthio, F, Cl, Br, I —CN, —NO$_2$, —OH, —O$R^7$, —$X^2$(CH$_2$)$_p$C(=O)N$R^9R^{10}$, —$X^2$(CH$_2$)$_p$C(=S)N$R^9R^{10}$, —X²(CH₂)ₚOC(=O)NR⁹R¹⁰, —X²(CH₂)ₚCO₂R⁷, —OC(=O)R⁷, —OC(=O)NHR¹², O-tetrahydropyranyl, —NR⁹R¹⁰, —NR⁸CO₂R⁷, —NR⁸C(=O)NR⁹R¹⁰, —NR⁸C(=S)NR⁹R¹⁰, —NHC(=NH)NH₂, —NR⁸C(=O)R⁷, —NR⁸C(=S)R⁷, —NR⁸S(=O)₂R⁷, —S(O)ᵧR⁷, —CO₂R¹², —C(=O)NR⁹R¹⁰, —C(=S)NR⁹R¹⁰, —C(=O)R¹², —CH₂OR⁸, —CH=NNR¹²R¹²ᴬ, —CH=NOR¹², —CH=NR⁷, —CH=NNHCH(N=NH)NH₂, —S(=O)₂NR¹²R¹²ᴬ, —P(=O)(OR⁸)₂, —OR¹¹, and a monosaccharide of 5 to 7 carbons where each hydroxyl group of the monosaccharide is independently either unsubstituted or is replaced by H, alkyl of 1 to 4 carbons, alkylcarbonyloxy of 2 to 5 carbons, or alkoxy of 1 to 4 carbons;

X² is O, S, or NR⁸;

Q is selected from —NR⁶, —O—, and —S—;

R⁶ is selected from H, —SO₂R⁷, —CO₂R⁷, —C(=O)R⁷, —C(=O)NR⁹R¹⁰, alkyl of 1–8 carbons, alkenyl of 2–8 carbons, and alkynyl of 2–8 carbons; and either
1) each alkyl, alkenyl, or alkynyl group is unsubstituted; or
2) each alkyl, alkenyl, or alkynyl group independently is substituted, as defined for R², R³, R⁴, and R⁵ in e) above;

Y is selected from:
a) an unsubstituted alkylene of 1–3 carbons;
b) an alkylene of 1–3 carbons substituted with R¹³, where R¹³ is selected from R¹², thioalkyl of 1–4 carbons, halogen, alkyl of 1–8 carbons, alkenyl of 2–8 carbons, and alkynyl of 2–8 carbons, where
 i) each alkyl of 1–8 carbons, alkenyl of 2–8 carbons, and alkynyl of 2–8 carbons is unsubstituted; or
 ii) each alkyl of 1–8 carbons, alkenyl of 2–8 carbons, and alkynyl of 2–8 carbons, independently, is substituted, as defined for R², R³, R⁴, and R⁵ in e) above; and
c) a functional group selected from —CH=CH—, —CH(OH)—CH(OH)—, —O—, —S—, —S(=O)—, —S(=O)₂—, —C(R⁶)₂—, —C=C(R¹³)₂—, —C(=O)—, —C=N(R¹³)—, —C(=NOR¹²)—, —C(OR¹²)R¹²—, —C(=O)CH(R⁶)—, —CH(R⁶)C(=O)—, —C(=NOR¹²)CH(R⁶)—, —CHR⁸C(=NOR¹²)—, —C(=O)N(R⁸)—, —N(R⁸)C(=O)—, —CH₂Z—, —ZCH₂—, and —CH₂ZCH₂—, where Z is selected from —C(R¹²)—, —O—, —S—, —CO₂R¹², —C(=NOR¹²)—, and —N(R¹²)—;

A¹ and A² are selected from H, H; H, OR¹²; H, —SR¹²; H, —N(R¹²)₂; and a group where A¹ and A² together form a moiety selected from =O, =S, and =NR¹²; and, B¹ and B² are selected from H H; H, —OR¹²; H, —SR¹²; H, —N(R¹²)₂; and a group where B¹ and B² together form a moiety selected from =O, =S, and =NR¹²; with the proviso that at least one of the pairs A¹ and A², or B¹ and B², form =O.

In certain preferred embodiments of the compounds of Formula I, R¹, R³, and R⁵ are H. In certain further preferred embodiments, —G—X—Y— is CH₂N(R¹)C(=O), C(=O)N(R¹)CH₂, or C(=O)N(R¹)C(=O).

In other preferred embodiments, rings B and F, independently, are substituted or unsubstituted phenyl or pyridyl. In other preferred embodiments, Q is —NR⁶, wherein the referred values for R⁶ are H and substituted or unsubstituted lower alkyl. In certain further preferred embodiments, Y is an unsubstituted alkylene of 1–3 carbons, —C(=O)—, —CH₂O—, —S—, —O—, or —CH=CH—.

In other preferred embodiments, the isomeric fused pyrrolocarbazoles are represented by the formula:

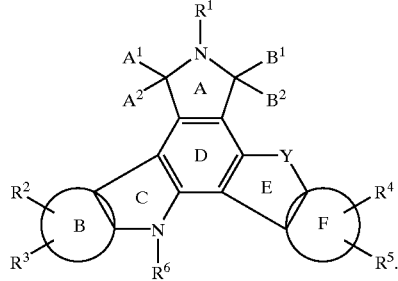

In certain further preferred embodiments, the isomeric fused pyrrolocarbazoles are represented by the formula:

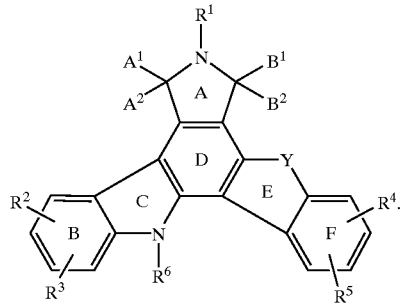

In certain preferred embodiments of these formula, R¹, R³ and R⁵ are H. In other preferred embodiments, A¹ and A² are selected from H, H; H, OH; H, OCH₃; H, —N(R¹²)₂; or a group where A¹ and A² together form =O or =NR¹²; B¹ and B² are selected from H, H; H, OH; H, OCH₃; H, —N(R¹²)₂; or a group where B¹ and B² together form =O or =NR¹²; and R¹² is H, methyl, ethyl, propyl, —OH, or methoxy. In other preferred embodiments, the referred values for R⁶ are H or substituted or unsubstituted lower alkyl. In other preferred embodiments, Y is an unsubstituted alkylene of 1–3 carbons, —C(=O)—, —CH₂O—, —S—, —O—, or —CH=CH—. Even further preferred embodiments are the compounds set forth in Tables 1 to 4.

In other embodiments, the present invention provides pharmaceutical compositions comprising a compound of Formula I and a pharmaceutically acceptable carrier. In a preferred composition, the compound of Formula I is one set forth in Table 1, 2, 3, or 4.

In certain preferred pharmaceutical compositions, the composition is for inhibiting one or more of trk kinase activity, VEGFR kinase activity, or PDGFR activity wherein the composition comprises a compound of Formula I and a pharmaceutically acceptable carrier. In other preferred pharmaceutical compositions the composition is for enhancing tropic factor or spinal chord ChAT activity wherein the composition comprises a compound of Formula I and a pharmaceutically acceptable carrier.

In other preferred pharmaceutical compositions, the composition is for treating or preventing prostate disorders such as prostate cancer or benign prostate hyperplasia In other preferred pharmaceutical compositions, the composition is for treating or preventing angiogenic disorders such as cancer of solid tumors, endometriosis, diabetic retinopathy, psoriasis, hemangioblastoma, ocular disorders or macular degeneration. In other preferred pharmaceutical compositions, the composition is for treating or preventing neoplasia, rheumatoid arthritis, pulmonary fibrosis, myelofibrosis, abnormal wound healing, atherosclerosis, or restenosis. In other preferred pharmaceutical compositions, the composition is for treating or preventing Alzheimer's disease, amyotrophic lateral sclerosis, Parkinson's disease, stroke, ischaemia, Huntington's disease, AIDS dementia, epilepsy, multiple sclerosis, peripheral neuropathy, or injuries of the brain or spinal chord.

In other embodiments, the present invention provides a method for inhibiting trk kinase activity comprising providing a compound of Formula I in an amount sufficient to result in effective inhibition. In a preferred embodiment, the compound of Formula I is provided to treat inflammation. In another preferred embodiment, the trk kinase receptor is trk A.

In other embodiments, the present invention provides a method for treating or preventing prostate disorders which comprises administering to a host in need of such treatment or prevention a therapeutically effective amount of a compound of Formula I. In a preferred embodiment, the prostate disorder is prostate cancer or benign prostate hyperplasia.

In other embodiments, the present invention provides a method for treating or preventing angiogenic disorders where VEGFR kinase activity contributes to pathological conditions, the method comprising providing a compound of Formula I in an amount sufficient to result in the vascular endothelial growth factor receptor being contacted with an effective inhibitory amount of the compound. In another embodiment, the present invention provides a method for treating or preventing angiogenic disorders which comprises administering to a host in need of such treatment or prevention a therapeutically effective amount of a compound of Formula I. In a preferred embodiment, the angiogenic disorder is cancer of solid tumors, ocular disorders, macular degeneration, endometriosis, diabetic retinopathy, psoriasis, or hemangioblastoma.

In other embodiments, the present invention provides a method for treating or preventing disorders where PDGFR activity contributes to pathological conditions, the method comprising providing a compound of Formula I in an amount sufficient to result in the platelet derived growth factor receptor being contacted with an effective inhibitory amount of the compound. In another embodiment, the present invention provides a method for treating or preventing pathological disorders which comprises administering to a host in need of such treatment or prevention a therapeutically effective amount of a compound of Formula I. In preferred embodiments, the pathological disorder is neoplasia, rheumatoid arthritis, pulmonary fibrosis, myelofibrosis, abnormal wound healing, atherosclerosis, or restenosis.

In other embodiments, the present invention provides a method for treating disorders characterized by the aberrant activity of trophic factor responsive cells, the method comprising providing a compound of Formula I in an amount sufficient to result in the trophic factor cell receptor being contacted with an effective activity inducing amount of the compound. In preferred embodiments, the activity of the trophic factor responsive cells is ChAT activity. In another embodiment, the present invention provides a method for treating or preventing Alzheimer's disease, amyotrophic lateral sclerosis, Parkinson's disease, stroke, ischaemia, Huntington's disease, AIDS dementia, epilepsy, multiple sclerosis, peripheral neuropathy, or injuries of the brain or spinal chord which comprises administering to a host in need of such treatment or prevention a therapeutically effective amount of a compound of Formula I. The compounds represented by Formula I may also be referred to as Compound I, and the same applies to the compounds of other formula numbers.

Definitions

The following terms and expressions have the indicated meanings. As used herein "stable compound" or "stable structure" is meant to indicate a compound that is sufficiently robust to survive isolation to a useful degree of purity from a reaction mixture, and preferably capable of formulation into an efficacious therapeutic agent The present invention is directed only to stable compounds. As used herein, "substituted" is intended to indicate that one or more hydrogen atoms on the indicated atom is replaced with a selected group referred to herein as a "substituent", provided that the substituted atom's valency is not exceeded, and that the substitution results in a stable compound.

As used herein, the term "alkyl" means a straight-chain, cyclic, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, hexyl, octyl, cyclopropyl, and cyclopentyl. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons.

Alkyl groups and alkyl moieties contained within substituent groups such as aralkyl, alkoxy, arylalkoxy, hydroxyalkoxy, alkoxy-alkoxy, hydroxy-alkylthio, alkoxyalkylthio, alkylcarbonyloxy, hydroxyalkyl and acyloxy groups may be substituted or unsubstituted. A substituted alkyl group has 1 to 3 independently-selected substituents, preferably hydroxy, lower alkoxy, lower alkoxy-alkoxy, substituted or unsubstituted arylalkoxy-lower alkoxy, substituted or unsubstituted heteroarylalkoxy-lower alkoxy, substituted or unsubstituted arylalkoxy, substituted or unsubstituted heterocycloalkoxy, halogen, carboxyl, lower alkoxycarbonyl, nitro, amino, mono- or di-lower alkylamino, dioxolane, dioxane, dithiolane, dithione, furan, lactone, or lactam.

As used herein, the term "alkenyl" is intended to include straight-chain, cyclic, or branched hydrocarbon chains having at least one carbon-carbon double bond. Examples of alkenyl groups include ethenyl, propenyl, 3-methylbutenyl, and cyclohexenyl groups. As used herein, the term "alkynyl" is intended to include straight-chain, cyclic, or branched hydrocarbon chains having at least one carbon-carbon triple bond. Examples of alkynyl groups include ethynyl, propynyl, 3-methylbutynyl, and cyclohexynyl groups.

As used herein, the "acyl" moiety of acyl-containing groups such as acyloxy groups is intended to include a straight-chain, branched, or cyclic alkanoyl group having 1 to 6 carbon atoms, such as formyl, acetyl, propanoyl, butyryl, valeryl, pivaloyl or hexanoyl.

As used herein, the term "carbocyclic" refers to cyclic groups in which the ring portion is composed solely of carbon atoms. These include, but are not limited to, cyclopropyl, cyclobutyl, cyclopentyl, cyclohexl, cycloheptyl, cyclooctyl. The terms "heterocyclo" and "heterocyclic" refer to cyclic groups in which the ring portion includes at least one heteroatom such as O, N, or S. Heterocyclyl groups include heteroaryl and heteroalkyl groups.

As used herein the term "aryl" means an aromatic ring having 6 to 12 carbon atoms such as phenyl, biphenyl and naphthyl. Preferred aryl groups include unsubstituted or substituted phenyl and naphthyl groups. The term "heteroaryl" as used herein denotes an aryl group in which one or more ring carbon atoms is replaced by a hetero (i.e., non-carbon) atom such as O, N or S. Preferred heteroaryl groups include pyridyl, pyrimidyl, pyrrolyl, furyl, thienyl, imidazolyl, triazolyl, tetrazolyl, quinolyl, isoquinolyl, benzoimidazolyl, thiazolyl, pyrazolyl, and benzothiazolyl groups. The term "heteroalkyl" denotes a cycloalkyl group in which one or more ring carbon atoms is replaced by hetero atoms such as O, N, or S.

As used herein, the term "aralkyl" (or "arylalkyl") is intended to denote a group having from 7 to 15 carbons, consisting of an alkyl group that bears an aryl group. Examples of aralkyl groups include, but are not limited to, benzyl, phenethyl, benzhydryl and naphthylmethyl groups. Substituted aryl, substituted heterocyclic and substituted aralkyl groups each have 1 to 3 independently selected substituents that are preferably lower alkyl, hydroxy, lower alkoxy, carboxy, lower alkoxycarbonyl, nitro, amino, mono- or di-lower alkylamino, and halogen.

Preferred heterocyclic groups formed with a nitrogen atom include pyrrolidinyl, piperidinyl, piperidino, morpholinyl, morpholino, thiomorpholino, N-methylpiperazinyl, indolyl, isoindolyl, imidazole, imidazoline, oxazoline, oxazole, triazole, thiazoline, thiazole, isothiazole, thiadiazoles, triazines, isoxazole, oxindole, indoxyl, pyrazole, pyrazolone, pyrimidine, pyrazine, quinoline, iosquinoline, and tetrazole groups. Preferred heterocyclic groups formed with an oxygen atom include furan, tetrahydrofuran, pyran, benzofurans, isobenzofurans, and tetrahydropyran groups. Preferred heterocyclic groups formed with a sulfur atom include thiophene, thianaphthene, tetrahydrothiophene, tetrahydrothiapyran, and benzothiophenes.

As used herein, "hydroxyalkyl" groups are alkyl groups that have a hydroxyl group appended thereto. As used herein, "hydroxyalkoxy" groups are alkoxy groups that have a hydroxyl group appended thereto. As used herein, "halogen" refers to fluorine, chlorine, bromine and iodine.

As used herein, the term "heteroarylalkyl" means an arylalkyl group that contains a heteroatom in the aryl moiety. The term "oxy" denotes the presence of an oxygen atom. Thus, "alkoxy" groups are alkyl groups that are attached through an oxygen atom, and "carbonyloxy" groups are carbonyl groups that are attached through an oxygen atom.

As used herein, the terms "heterocycloalkyl" and "heterocycloalkoxy" mean an alkyl or an alkoxy group that has a heterocyclo group attached to the alkyl moiety thereof, and the term "arylalkoxy" means an alkoxy group that has an aryl group attached to the alkyl moiety thereof As used herein, the term "alkylcarbonyloxy" means a group of formula —O—C(=O)-alkyl.

As used herein, the term "alkyloxy-alkoxy" denotes an alkoxy group that contains an alkyloxy substituent attached to its alkyl moiety. The term "alkoxy-alkylthio" means an alkylthio group (i.e., a group of formula —S-alkyl) that contains an alkoxy substituent attached to its alkyl moiety. The term "hydroxy-alkylthio" means an alkylthio group (i.e., a group of formula —S-alkyl) that contains a hydroxy substituent attached to its alkyl moiety.

As used herein, the term "monosaccharide" has its accustomed meaning as a simple sugar. As used herein, the term "amino acid" denotes a molecule containing both an amino group and a carboxyl group. Embodiments of amino acids include α-amino acids; i.e., carboxylic acids of general formula HOOC—CH(NH2)-(side chain). Side chains of amino acids include naturally occurring and non-naturally occurring moieties. Non-naturally occurring (i.e., unnatural) amino acid side chains are moieties that are used in place of naturally occurring amino acid side chains in, for example, amino acid analogs. See, for example, Lehninger, Biochemistry, Second Edition, Worth Publishers, Inc, 1975, pages 73–75, incorporated by reference herein. In certain embodiments, substituent groups for the compounds of Formulas I, II, and III include the residue of an amino acid after removal of the hydroxyl moiety of the carboxyl group thereof; i.e., groups of Formula —C(=O)CH(NH$_2$)-(side chain).

Functional groups present on the compounds of Formula I may also contain protecting groups. Preferred protecting groups include the benzyloxycarbonyl (Cbz; Z) group and the tert-butyloxycarbonyl (Boc) group. Other preferred protecting groups may be found in Greene, T. W. and Wuts, P. G. M., *Protective Groups in Organic Synthesis* 2d. Ed., Wiley & Sons, 1991, the disclosure of which is incorporated herein by reference.

As used herein, terms commonly used to describe the effects of therapeutic agents in biological systems, assays, and the like, are intended to have their art-recognized meanings. As used herein, the term "effect" when used to modify the terms "function" and "survival" means a positive or negative alteration or change. An effect which is positive may be referred to herein as an "enhancement" or "enhancing", and an effect which is negative may be referred to herein as "inhibition" or "inhibiting."

As used herein, the terms "enhance" or "enhancing" when used to modify the terms "function" or "survival" means that the presence of an isomeric fused pyrrolocarbazole or isoindolone compound has a positive effect on the function and/or survival of a trophic factor responsive cell compared with a cell in the absence of the compound. For example, and without limitation, with respect to the survival of, e.g., a cholinergic neuron, the compound would evidence enhancement of survival of a cholinergic neuronal population at risk of dying (due to, e.g., injury, a disease condition, a degenerative condition or natural progression) when compared to a cholinergic neuronal population not presented with such compound, if the treated population has a comparatively greater period of functionality than the non-treated population.

As used herein, "inhibit" and "inhibition" mean that a specified response of a designated material (e.g., enzymatic activity) is comparatively decreased in the presence of an isomeric fused pyrrolocarbazole or isoindolone compound.

As used herein, the term "trk" refers to the family of high affinity neurotrophin receptors presently comprising trk A, trk B, and trk C, and other membrane associated proteins to which a neurotrophin can bind.

As used herein, the terms "cancer" and "cancerous" refer to any malignant proliferation of cells in a mammal. Examples include prostate, benign prostate hyperplasia, ovarian, breast, brain, lung, pancreatic, colorectal, gastric, stomach, solid tumors, head and neck, neuroblastoma, renal cell carcinoma, lymphoma, leukemia, other recognized malignancies of the hematopoietic systems, and other recognized cancers.

As used herein the terms "neuron," "cell of neuronal lineage" and "neuronal cell" include, but are not limited to, a heterogeneous population of neuronal types having singular or multiple transmitters and/or singular or multiple functions; preferably, these are cholinergic and sensory neurons. As used herein, the phrase "cholinergic neuron" means neurons of the Central Nervous System (CNS) and Peripheral Nervous System (PNS) whose neurotransmitter is acetylcholine; exemplary are basal forebrain, striatal, and spinal cord neurons. As used herein, the phrase "sensory neuron" includes neurons responsive to environmental cues (e.g., temperature, movement) from, e.g., skin, muscle and joints; exemplary is a neuron from the dorsal root ganglion.

As used herein, a "trophic factor-responsive cell," is a cell which includes a receptor to which a trophic factor can specifically bind; examples include neurons (e.g., cholinergic and sensory neurons) and non-neuronal cells (e.g., monocytes and neoplastic cells).

As used herein, a "therapeutically effective amount" refers to an amount of a compound of the present invention effective to prevent or treat the symptoms of particular disorder. Such disorders include, but are not limited to, those pathological and neurological disorders associated with the aberrant activity of the receptors described herein, wherein the treatment or prevention comprises inhibiting, inducing, or enhancing the activity thereof by contacting the receptor with a compound of Formula I.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ration.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

As used herein, "prodrug" is intended to include any covalently bonded carriers which release the active parent drug according to Formula (I) or other formulas or compounds of the present invention in vivo when such prodrug is administered to a mammalian subject. Since prodrugs are known to enhance numerous desirable qualities of pharmaceuticals (e.g., solubility, bioavailability, manufacturing, etc.) the compounds of the present invention may be delivered in prodrug form. Thus, the present invention contemplates prodrugs of the claimed compounds, compositions containing the same, and methods of delivering the same. Prodrugs of a compound of the present invention, for example Formula I, may be prepared by modifying functional groups present in the compound in such a way that the modifications are cleaved, either in routine manipulation or in vivo, to the parent compound. Accordingly, prodrugs include, for example, compounds of the present invention wherein a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

Synthesis

The compounds of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization; and the like, or by chiral synthesis either from chiral starting materials or by deliberate synthesis of target chiral centers.

As will be readily understood, functional groups present on the compounds of Formula I may contain protecting groups during the course of synthesis. For example, the amino acid side chain substituents of the compounds of Formula I can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl (Cbz; Z) group and the tert-butyloxycarbonyl (Boc) group. Other preferred protecting groups according to the invention may be found in Greene, T. W. and Wuts, P. G. M., *Protective Groups in Organic Synthesis* 2d. Ed., Wiley & Sons, 1991.

Compounds of the present invention may be prepared as outlined in the following schemes. Generally, imide compounds may be prepared as shown in Scheme 1.

Scheme 1

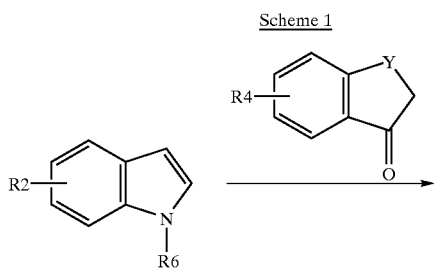

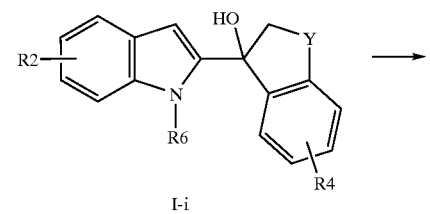

I-i

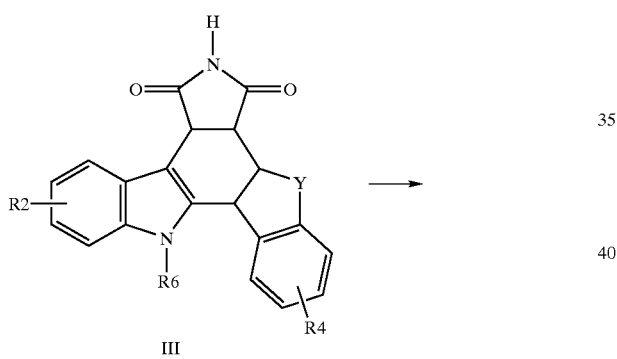

II

III

IV

A cycloaddition reaction with maleimide and a cyclic-2-vinyl derivative (II) gives the tetrahydrocarbazole compounds of general structure (III), which can be dehydrogenated by methods well known in the art (Scheme 1). The cycloaddition reaction may be carried out in the absence of a solvent at temperatures of about 150 to about 200° C., or in a solvent such as toluene, xylene or chlorobenzene at elevated temperatures with or without an added Lewis acid catalyst. The dienes of general structure (II) may be prepared by addition of a 2-lithio indole species, substituted or unsubstituted, to a cyclic (hetero)aryl 1-ketone, for example, 1-indanone, 1-tetralone, 4-chromanone, 4-keto-4,5,6,7-tetrahydrothianaphthlene, substituted or unsubstituted, as described, for example, in *Tetrahedron Lett.* 1985, 26, 5935, the disclosure of which is hereby incorporated by reference.

Scheme 2 outlines the general approach for preparing lactam isomers, i.e., compounds wherein G—X—W is —C(=O)—N(R$^1$)—C(B$^1$B$^2$)— or —C(A$^1$A$^2$)—N(R$^1$)—C(=O)—.

Scheme 2

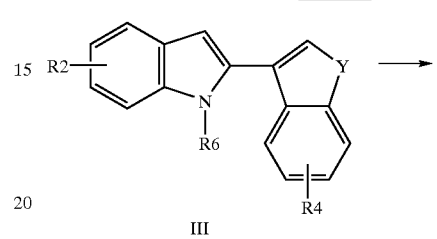

III

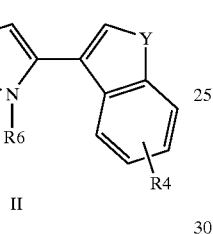

+

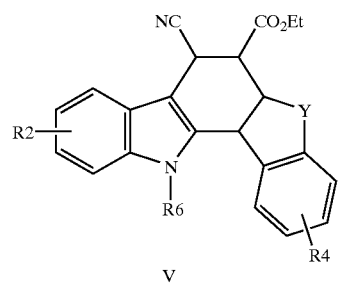

V

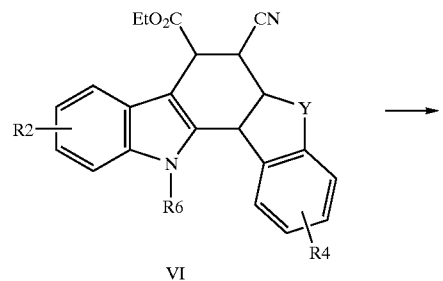

VI

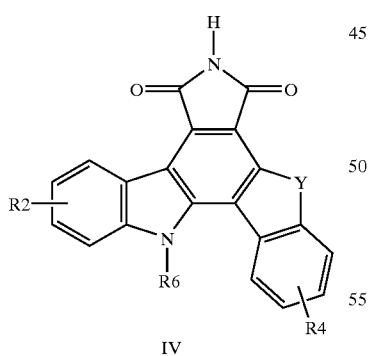

+

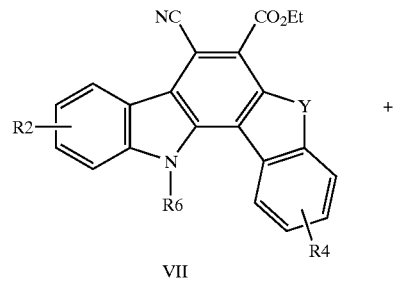

VII

VIII

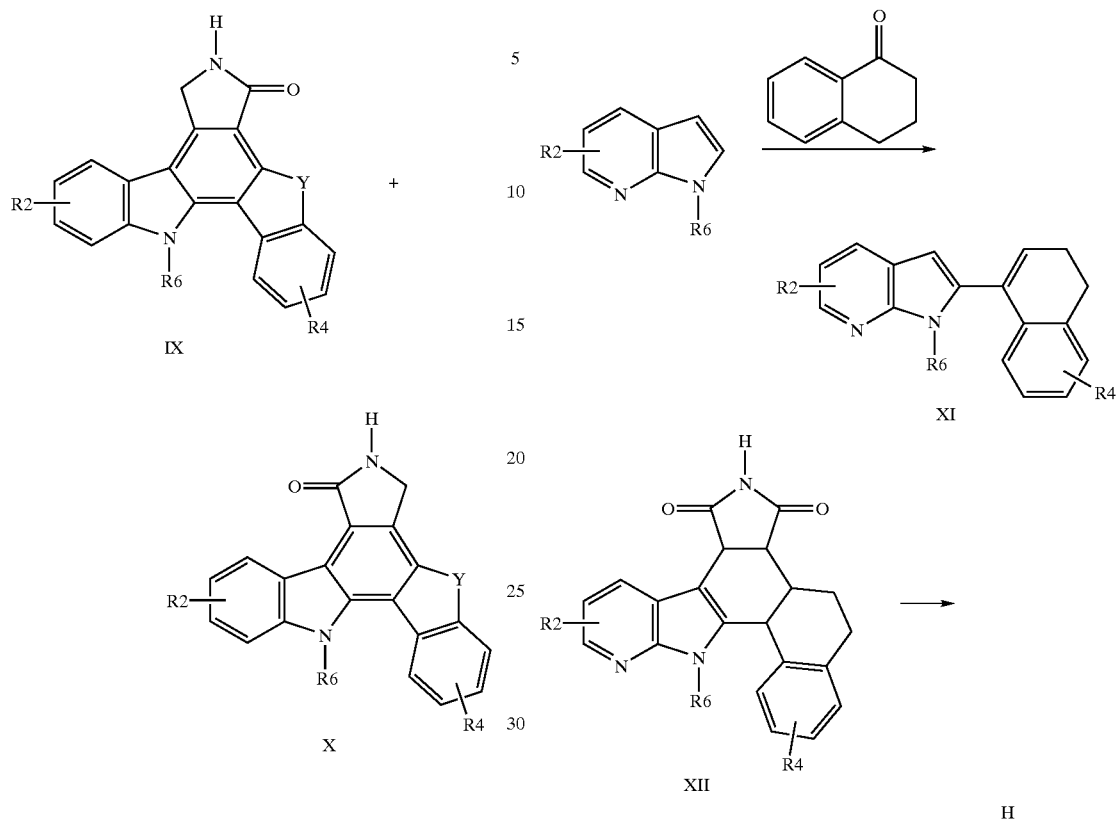

Cycloaddition reaction of dienes of general structure III with ethyl cis-β-cyanoacrylate under conditions described for imides in Scheme 1 produces the cyanoester tetrahyrocarbazole regioisomers of general structures V and VI. Standard procedures such as recrystallization or chromatography may be used to separate the resulting regioisomers V and VI. The tetrahydrocarbazole cyano-esters may be readily dehydrogenated according to conventional processes with, for example, 2,3-dichloro-4,5-dicyano-1,4-benzoquinone to produce the aromatized carbazoles of general structure VII and VIII (Scheme 2). Lactams of general structure IX and X may be prepared separately or as a mixture by reductive cyclization of the nitrile-esters using reducing agents, for example, raney nickel/$H_2$, PdO, and Pd or Pt on activated charcoal. The imide derivative IV may also be readily be reduced to lactam isomers IX and X by conventional processes such as zinc amalgam-HCl, Zn in acetic acid, or by treatment with hydride reducing agents such as lithium aluminum hydride. Standard processes such as recrystallization or chromatography may separate the resulting lactam regioisomers.

Compounds in which G—X—W is —CH($R^{1A}$)—C(=O)—N($R^1$)— or —N($R^1$)—C(O)—CH($R^{1A}$)—, as well as those in which G—X—W is a lactam or imide can be prepared by methods taught, for example, in U.S. Pat. Nos. 5,616,724, and 5,801,190, the disclosures of which is hereby incorporated herein by reference in its entirety.

Compounds containing heteroaryl groups in rings B or F may be prepared using the described methods as demonstrated in Schemes 3 and 4. The phenyl ring of the indole may be a heterocycle, for example, but not limited to, 7-azaindole.

Scheme 4

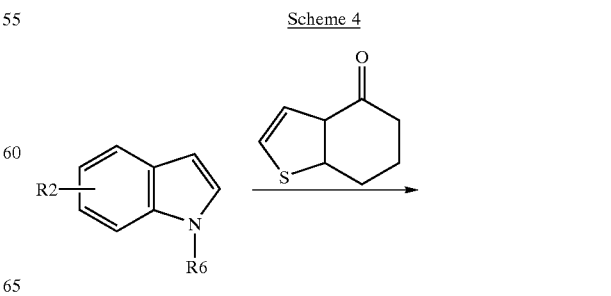

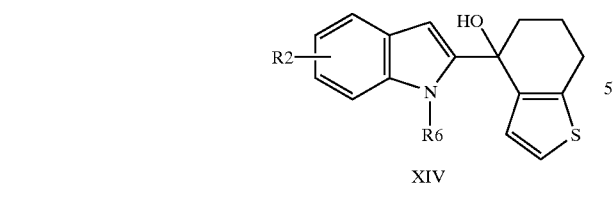

XIV

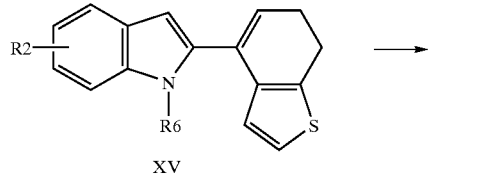

XV

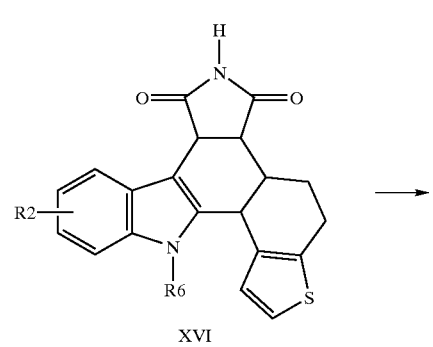

XVI

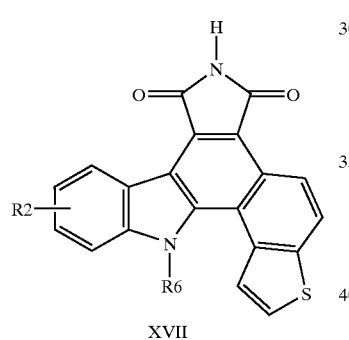

XVII

Although the resulting alcohol derivative of general structure (I-i) shown in Scheme 1 may be dehydrated to compounds of general structure (II) using conditions known in the art such as HCl in acetone or p-toluenesulfonic acid in benzene, dienes of general structure (II) may be also be prepared using palladium catalyzed cross coupling methodology. For example, coupling an appropriate bromo, iodo or a trifluoromethane sulfonate derivative with a 2-stannyl- or 2-boronicacid indole derivative as shown in Scheme 5.

Scheme 5

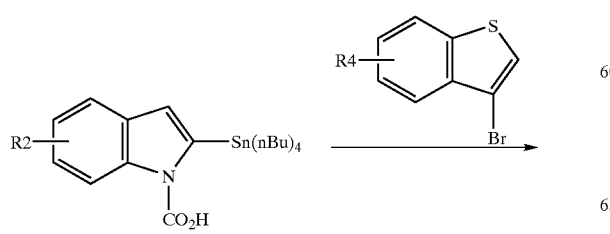

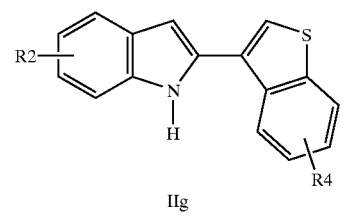

IIg

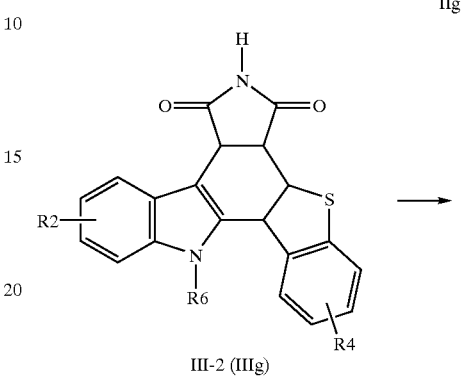

III-2 (IIIg)

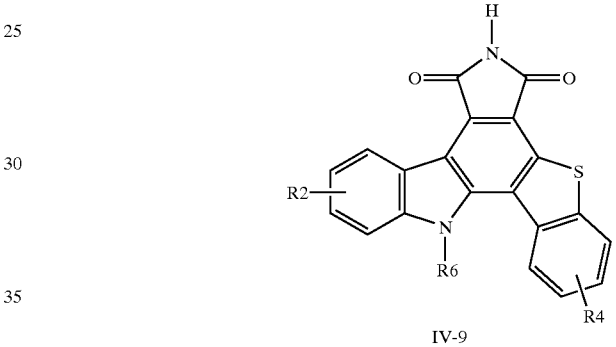

IV-9

The tetrahydrocarbazole cycloaddition adducts m can be readily dehydrogenated according to conventional processes with, for example, with 2,3-dichloro-4,5-dicyano-1,4-benzoquinone to give the aromatized carbazoles of general structure IV (Scheme 1).

Scheme 6

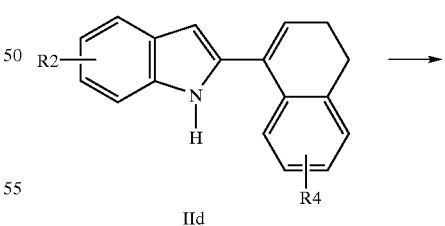

IId

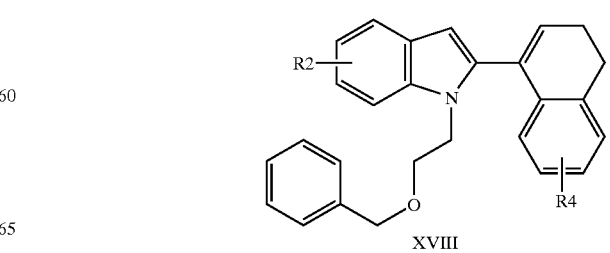

XVIII

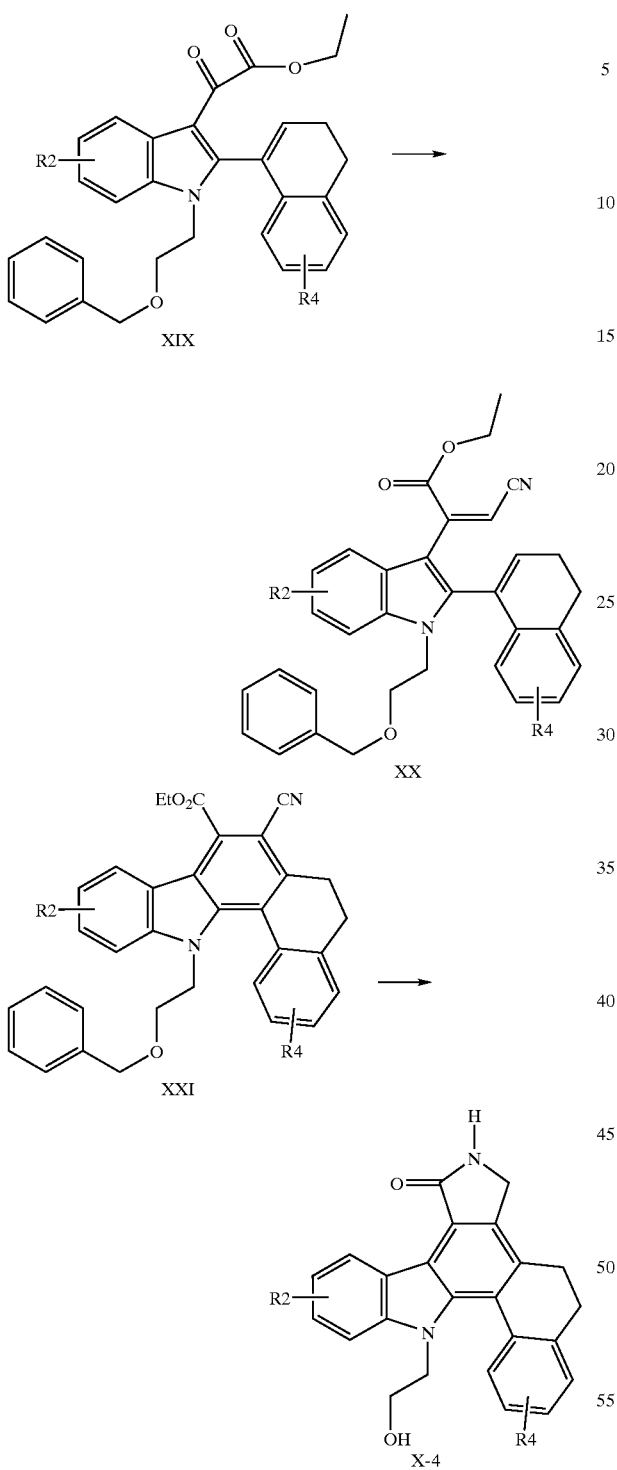

cyano-ester carbazole of general structure XXI (Scheme 6) or VIII (Scheme 2). Reductive cyclization produces the lactam of general structure X (Scheme 2, 6).

Compounds of the present invention in which general structures IV, IX or X have Y=CH$_2$ may be further substituted as shown in Scheme 7.

Scheme 7

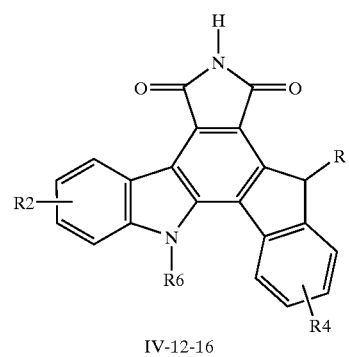

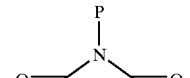
1) RMgX or Cs$_2$CO$_3$
   RX or RCHO
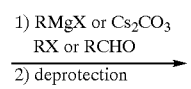
2) deprotection

P = protection group

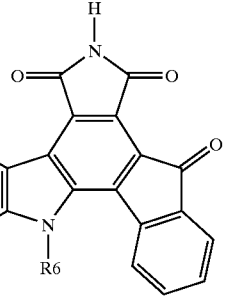

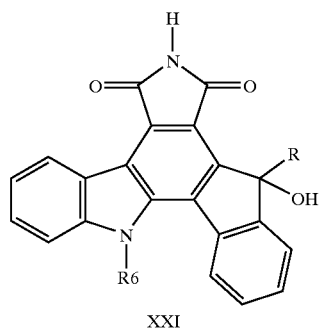

Scheme 6 outlines an alternative method to prepare lactam isomer of general structure X. A diene of general structure II, substituted or unsubstituted, is reacted with oxalyl chloride and an alcohol to produce keto-esters of general structure XIX. Olefination reactions known to those skilled in the art of organic synthesis, for example, reaction of ketone XIX with diethyl cyanomethylphosphonate, readily produces cyano-ester XX. Aromatic ring closure, under palladium catalyzed or oxidative conditions gives the

Scheme 8

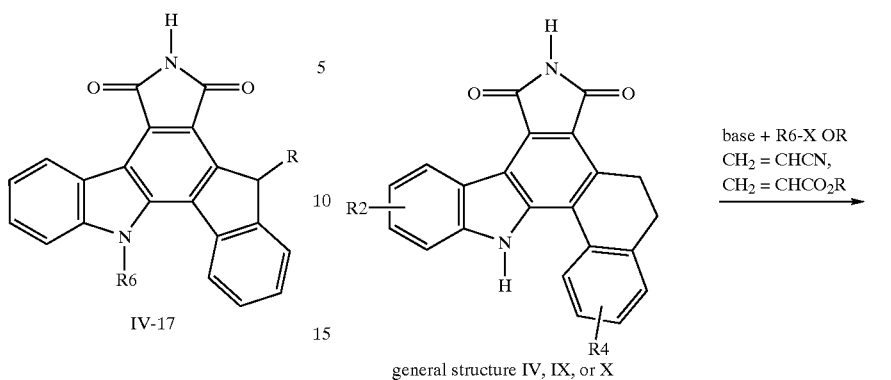

Generally, compounds in which $R^6$ is hydrogen, can be alkylated in the presence of base (e.g., hydrides, alkoxides, hydroxides of alkali or alkaline earth metals, or of organolithium compounds) by treatment with $R^6L$ in which L is a leaving group such as a halogen. The resulting pyrrolocarbazole may have an alkyl group, substituted or unsubstituted bound to the indole nitrogen, for example IV-20, 41. Compounds of general formula IV, IX or X, in which $R^6$ is N-hydrogen may be subjected to Michael reaction conditions using a base, such as DBU and a Michael acceptor, such as an acrylic acid derivative or acrylonitrile to produce compounds IV-20-22. Reactions of this type may be further understood by reference to Scheme 8.

Halo derivatives, such as bromine subsituted compound IV-9 may be used to further modify the indole ring as shown in Schemes 9 and 10.

Scheme 9

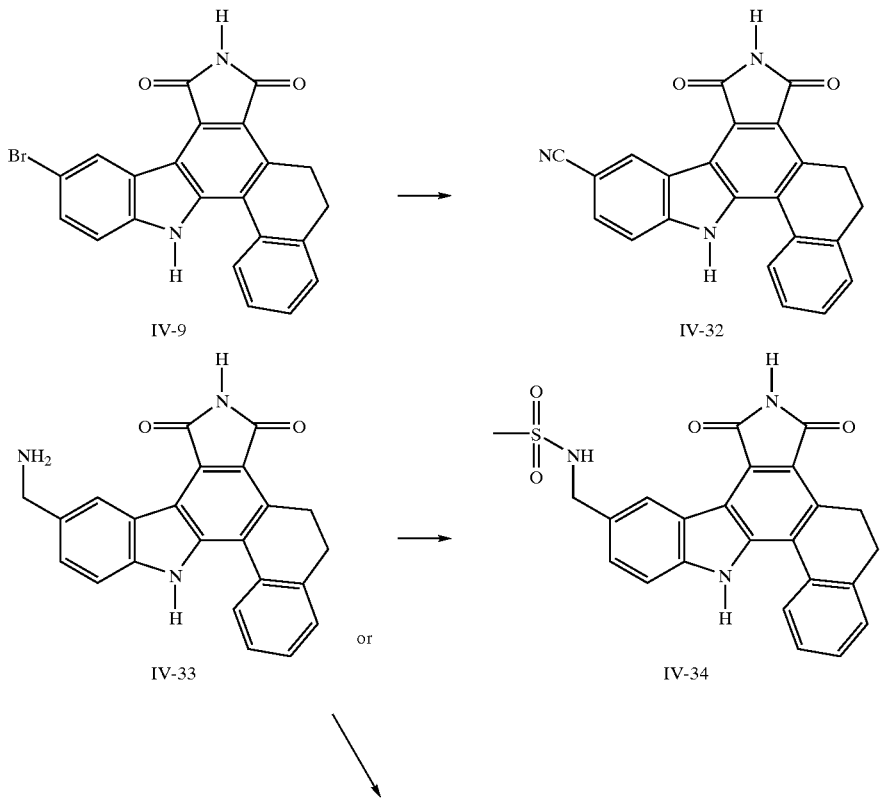

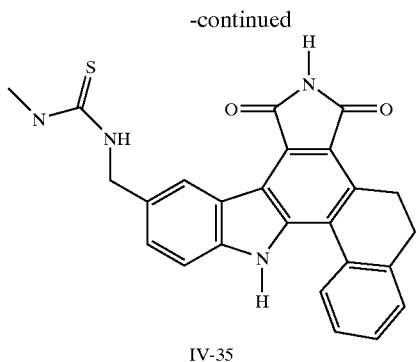

IV-35

Palladium catalysed Heck reaction using IV-9 and a coupling partner such as a vinyl aryl or herteroaryl derivative, acrylic acid derivative or acrylonitrile produces vinyl derivatives IV-36, 37, 39, 43. The vinyl derivative may be reduced to the alkane derivatives such as IV-38, 40 using reducing conditions such as Palladium on carbon under a hydrogen atmosphere.

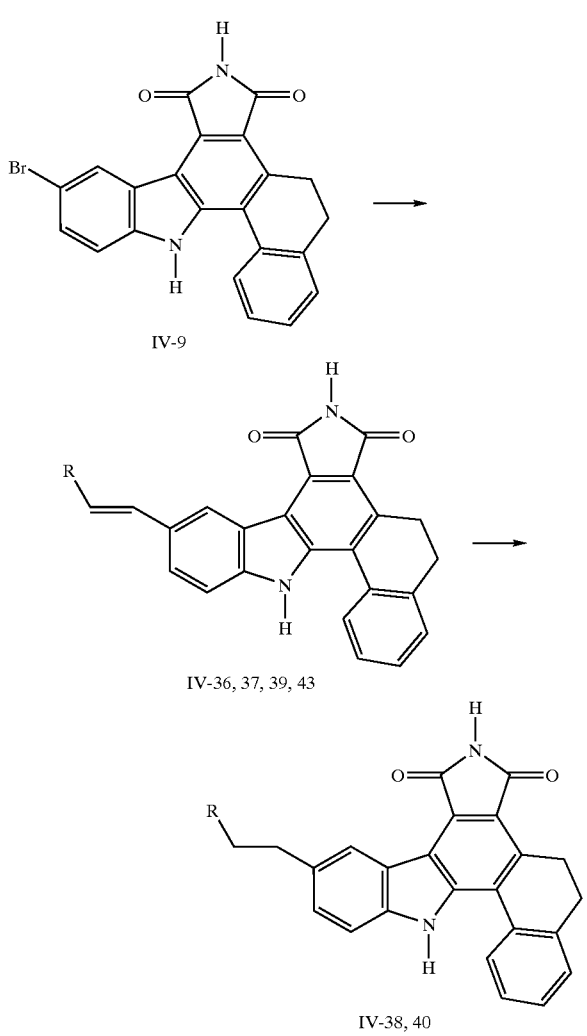

Scheme 10

IV-9

IV-36, 37, 39, 43

IV-38, 40

Other features of the invention will become apparent in the course of the following descriptions of exemplary embodiments. These examples are given for illustration of the invention and are not intended to be limiting thereof.

EXAMPLES

Certain abbreviations used herein are defined as follows: "THF" for tetrahydrofuran, "BuLi" for butyl lithium, "NMP" for N-methyl pyrrolidinone, "DMSO" for dimethylsulfoxide, "CDCl$_3$" for deuterated chloroform, "RaNi" for raney nickel, "TLC" for thin layer chromatography, "EtOAc" for ethyl acetate, "TBAF" for tetrabutylammonium fluoride, "ca" for approximately, "rt" for room temperature, "psi" for pounds per square inch, "mm" for millimeters of Hg, "° C." for degrees Celsius, "d" for doublet, "dd" for doublet of doublets, "t" for triplet, "m" for multiplet, "eq" for equivalents, "g" for gram or grams, "mg" for milligram or milligrams, "mL" for milliliter or milliliters, "H" for hydrogen or hydrogens, "hr" or "h" for hour or hours, "m" for multiplet, "M" for molar, "min" or "m" for minute or minutes, "MHz" for megahertz, "mp" for melting point, "MS" for mass spectroscopy, "nmr" or "NMR" for nuclear magnetic resonance spectroscopy.

Example 1

Compound IV-1

Step 1: Intermediate I-ia (Y=CH$_2$, R$^2$=R$^4$=H, R$^6$=H (2-(1-Hydroxy)indanyl)indole))

To a solution of indole (4.0 g, 34.1 mmol) in THF (200 mL) at −78° C. under a nitrogen atmosphere was added BuLi (34.1 mmol, 13.7 mL of 2.5 M solution in hexanes) dropwise over 15 min. Following stirring 30 min, CO$_2$(g) was passed through the solution for 10 min after which the clear solution was allowed to warm to ambient temperature, then concentrated to half volume at reduced pressure. The volume of THF was brought to about 200 mL and cooled to −78 C. t-BuLi (34.1 mmol, 20 mL of 1.7 M solution in hexanes) was added slowly while maintaining the temperature below −68° C. followed by stirring for 2 h at −78° C. I-Indanone (5.0 g, 37.4 mmol) in T1F (25 mL) was added, the mixture stirred for 1 h, quenched by addition of water (5 mL), then poured into saturated NH$_4$Cl solution (250 mL). The mixture was extracted with ether (1×200 mL), washed with 100 mL saturated NH$_4$Cl, dried (MgSO$_4$), and concentrated at reduced pressure to give an oil. Recrystallization from Et$_2$O-hexane gave 5.1 g (63%) of I-i-a, mp 123–124° C. $^1$H NMR (CDCl$_3$): δ2.3–2.5 (m, 1H), 2.55–2.7 (m, 2H), 2.9–3.05 (m, 1H), 3.1–3.2 (m, 1H), 6.15, s, 1H), 7.05–7.4 (m, 7H), 7.5 (d, 1H), 8.5 (s, 1H).

Step 2: Intermediate IIa (Y=CH$_2$, R$^2$=R$^4$=H, R$^6$=H (2-(I1-Indenyl)indole))

A stirred solution of Ia (4.0 g, 16.1 mmol) in acetone (50 mL) was added 2 N HCl (5 mL). After stirring 15 min at room temperature water was added and the solid collected by filtration, washed well with water and dried to give 3.7 g (100%) of intermediate IIa as a white solid. $^1$H NMR (CDCl$_3$): δ3.6 (s, 2H), 6.75 (s, 1H), 6.95 (s, 1H) 7.1–7.5 (m, 5H), 7.6 (d, 1H), 7.7 (d, 1H), 7.9 (d, 1H), 8.35 (bs, 1H). MS (ES$^+$) m/e 254 (M+23).

Step 3: Intermediate IIIa, (Y=CH$_2$, R$^2$=R$^4$=H, R$^6$=H)

A mixture of intermediate IIa (660 mg, 2.9 mmol) and maleimide (550 mg, 5.7 mmol) in a 10 cm sealed reaction vial was heated with stirring at 180–190° C. for 30 min. After cooling to about 50–60° C. MeOH (3 mL) was added and the product was collected after triturating to give 880 mg (92%) of ma as a white solid; mp 210–214° C. $^1$H NMR (DMSO-d$_6$, 300 MHz): δ3.1–3.4 (m, 2H), 3.8 (m, 2H), 3.95 (t, 1H), 4.35 (d, 1H), 6.9–7.4 (m, 7H), 7.75 (d, 1H), 11.05 (s, 1H), 11.25 (s, 1H) MS(ES$^-$): m/e 327 (m−1).

Step 4: Compound IV-1

To a suspension of intermediate ma (500 mg, 1.52 mmol) in toluene (60 mL) was added solid 2,3-dichloro-5,6-dicyano-1,4-benzoquinone (865 mg, 3.81 mmol) in one portion. The solution was maintained at 60–65° C. for 6 hours. After cooling on an ice bath, the solids were collected by filtration, suspended in MeOH (20 mL) and the product collected by filtration. Recrystallization from acetone gave 350 mg (71%) of compound IV-1 as a yellow solid, mp>300° C. 1H NMR (DMSO-d$_6$, 300 MHz): δ4.38 (s, 2H), 7.38 (t, 1H), 7.45–7.5 (m, 1H), 7.6–77 (m, 2H), 7.8 (m, 2H), 8.6 (d, 1H), 8.95 (d, 1H), 11.15 (s, 1H), 12.15 (s, 1H). MS(FAB): m/e 324 (m$^+$). Anal. calc. for C$_{21}$H$_{12}$N$_2$O$_2$·0.7H$_2$O: C, 74.86; H, 4.01; N, 8.31. Found; C, 74.85; H, 3.62; N, 8.52.

Example 2

Compound IV-2

To a stirred solution of Compound IV-I in NMP (2 mL) was added NaH (10 mg of 95%) at room temperature. The reaction turned from orange to green in color. After 0.5 h, water was added and the resulting red solid was collected, washed with water, and dried. $^1$H NMR (DMSO-d$_6$, 300 MHz): δ7.34 (t, 1H), 7.45 (t, 1H), 7.6–7.75 (m, 4H), 8.35 (d, 1H), 8.95 (d, 1H). MS(ES$^-$): m/e 337 (m−1).

Example 3

Compound IX-1

Step 1: Intermediate Va (Y=CH$_2$, R$^2$=R$^4$=H, R$^6$=H)

Intermediate IIa (2.0 g, 8.7 mmol) and ethyl cis-p-cyanoacrylate (3.3 g, 26.0 mmol) were heated in a round bottom flask under a stream of nitrogen at 190° C. with stirring for 1 h. While cooling to room temperature MeOH (10 mL) was added and stirring was continued for 0.5 h. The solution remained at freezer temperature overnight and the solid which separated was collected to give 880 mg (28%) of intermediate Va as a white solid. $^1$H NMR (DMSO-d$_6$, 300 M): δ1.28 (t, J=6.9 Hz, 3H), 3.00–3.08 (m, 1H), 3.30 (m, 1H), 3.47–3.51 (m, 1H), 3.62 (m, 1H), 4.26 (q, J=7.0 Hz, 2H), 4.54 (m, 1H), 4.72 (m, 1H), 6.97–7.09 (m, 2H), 7.16–7.24 (m, 3H), 7.31 (d, J=7.8 Hz, 1H), 7.50 (d, J=7.5H, H), 7.82 (d, J=7.0 Hz, 1H), 11.04 (s, 1H). MS (ES$^+$) m/e 357, 379 (M+1, M+23).

Step1b: The methanol layer from step 1a was concentrated at reduced pressure to an oil and the excess cyanoacrylate was removed by Kugelrohr distillation (oven temperature 80° C., 1 mm). The residue was triturated with ether to a yellow solid, which was collected. $^1$H NMR showed a 2:1 mixture of isomers Va and VIa (Y=CH$_2$); MS (ES$^+$) m/e 357, 379 (M+1, M+23).

Step 2: Intermediate VIIa (Y=CH$_2$, R$^2$=R$^4$=H, R$^6$=H)

To a suspension of intermediate VIa from step 1a (650 mg, 1.8 mmol) in toluene (60 mL) was added solid 2,3-dichloro-5,6-dicyano-1,4-benzoquinone (1.05 g, 4.6 mmol) in one portion. The solution placed in an oil bath at 65° C. for 6 h. After cooling at freezer temperature, the solids were collected by filtration, suspended in MeOH (20 mL) and the product collected by filtration to give 620 mg (98%) of a yellow solid. $^1$H NMR (DMSO-d$_6$, 300 MHz): δ1.44 (t, J=7.0 Hz, 3H), 4.36 (s, 2H), 4.45 (q, J=7.18 Hz, 2H), 7.38 (t, 1H), 7.44 (t, 1H), 7.54–7.63 (m, 2H), 7.71–7.78 (m, 2H), 8.55 (d, J=7.5 Hz, 1H), 8.63 (d, H=8.0 Hz, 1H), 12.22 (s, 1H). MS (ES$^+$) m/e 353, 375 (M+1, M+23).

Step 3: Compound IX-1

The product from step 2 (intermediate VIIa) (500 mg, 1.4 mmmol) in DMF (40 mL) and RaNi catalyst (1 small spatula) was hydrogenated at 60 psi on a Parr Apparatus for 24 h or until TLC (2:1. EtOAc:Hexanes) showed completion of reaction. The solvent was filtered through celite to remove catalyst then concentrated at reduced pressure. The solid was triturated with MeOH, collected and dried to give 325 mg (71%) of compound IX-1 as a white solid, mp>300° C. $^1$H NMR (DMSO-d$_6$, 300 MHz): δ4.30 (s, 2H), 4.93 (s, 2H), 7.32–7.42 (m, 2H), 7.52–7.56 (m, 2H), 7.72–7.76 (m, 2H), 8.05 (d, 1H), 8.51–8.54 (m, 2H), 11.92 (s, 1H). MS(FAB): m/e 311 (m$^+$).

Example 4

Compound X-1

Step 1: Intermediate VIIIa (Y=CH$_2$, R$^2$=R$^4$=H, R$^6$=H)

To a suspension of the cyano-ester isomers Va and VIa from example 3 step 1b (880 mg, 2.3 mmol) suspended in toluene (50 mL) was added solid 2,3-dichloro-5,6-dicyano-1,4-benzoquinone (1.3 g, 5.6 mmol) in one portion. The solution was placed in an oil bath at 65° C. for 6 h. After cooling at freezer temperature, the solids were collected by filtration, suspended in MeOH (20 mL) and the product collected by filtration to give 700 mg (88%) as a mixture of two cyano-ester carbazole isomers in a ratio of approximately 2:1 (VIIIa:VIIa) by $^1$H NMR. MS (ES$^+$) m/e 353 (M+1). The mixture was used directly in the next step.

Step 2: Compound X-1

A mixture of the cyano ester isomers VIIIa and VIIa from step 1 (700 mg, 2.0 mmmol) and RaNi catalyst (one spatula full) in DMF (40 mL) was hydrogenated at 60 psi on a Parr apparatus for 24 h or until TLC (2:1, EtOAc:Hexanes) showed completion of reaction. The solvent was filtered through celite to remove catalyst, then concentrated at reduced pressure. The product was triturated with MeOH, collected and dried to give 550 mg (89%) of a white solid. $^1$H NMR (DMSO-d$_6$, 300 MHz) showed a 2:1 mixture of compound X-1:I X-1. The compound X-1 was isolated by column chromatography (silica gel) and eluted with toluene:THF, increasing the THF from 30% to 50%. Fractions showing pure product were combined and concentrated at reduced pressure. The product was collected after triturated with MeOH mp>300° C. $^1$H NMR (DMSO-d$_6$, 300 MHz): δ4.08 (s, 2H), 4.59 (s, 2H), 7.20 (t, J=7.5 Hz, 1H), 7.37–7.46 (m, 2H), 7.54 (t, J=7.5 Hz, 1H), 7.64–7.7.71 (m, 2H), 8.53–8.56 (s, 2H) 9.18 (d, J=7.8 Hz, 1H), 11.71 (s, 1H). MS (ES$^+$): m/e 311 (M+1).

Example 5

Compound III-1

Step 1: Intermediate I-ib (Y=CH$_2$, R$^2$=R$^4$=H, R$^6$=H (1-Methyl-2-[(1hydroxy)indanyl)]indole))

BuLi (9.6 mL, 24.1 mmol) was added slowly to 1-methylindole (3.0 g, 22.9 mmol) in ether (20 mL). The solution was stirred at reflux 4 h, cooled to room temperature, followed by addition of I-indanone in 10 mL ether. After stirring at room temperature for 2 h, the solution was poured into a saturated NH$_4$Cl solution (30 mL). The ether layer was washed with water (2×20 mL), NaCl solution (2×20 mL) and dried (MgSO$_4$). Trituration with ether-hexane (2:1) gave 3.7 g (62%) of Ib. $^1$H NMR (DMSO-d$_6$, 300 MHz): δ2.5–2.6 (m, 1H), 2.7–2.8 (m, 1H), 2.9–3. (m, 1H), 3.1–3.2 (m, 1H), 3.95 (s, 3H), 6.0 (s, 1H), 7.05–7.30 (m, 2H), 7.45–7.5 (m, 7H).

Step 2: 1-Methyl-2-(1-indenyl)indole (Intermediate IIb)

A stirred solution of intermediate I-ib (500 mg, 1.9 mmol) in acetone was added 2 N HCl slowly at room temperature. After 2 h water was added and the precipitate collected by filtration, washed well with water and dried to give 445 mg (96%) intermediate IIb of a white solid mp>250° C. $^1$H NMR (CDCl$_3$): δ3.66 (s, 2H), 3.8 (s, 3H), 6.65 (s, 1H), 6.70 (s, 1H), 7.15–7.4 (m, 7.5–7.6 (m, 2H), 7.75 (d, 1H). MS (ES$^1$) m/e 245 (M-1).

Step 3: Compound III-1 (Intermediate IIIb, Y=CH$_2$, R$^2$=R$^4$=H, R$^6$=H)

A mixture of IIb (380 mg, 1.6 mmol) and maleimide (190 mg, 1.9 mmol) in a 10 cm sealed reaction vial was heated at 180° C. for 30 min. After allowing the mixture to cool below 60° C., MeOH (3 mL) was added and the product collected after triturating to give 450 mg (82%) of a white solid, mp 205–210° C. $^1$H NMR (DMSO-d$_6$, 300 M): δ2.9–295 (m, 1H), 3.05–3.15 (m, 2H), 3.5 (m, 1H), 3.9 (s, 3H), 7.0–7.3 (m, 5H), 7.45 (d, 1H), 7.55 (m, 1H), 7.85 (d, 1H), 11.05 (s 1H). MS (ES$^-$) m/e 341 (M-1).

Example 6

Compound W-3

To a suspension of compound III-1 from example 5 (330 mg, 1.0 mmol) in toluene (50 mL) was added solid 2,3-dichloro-5,6-dicyano-1,4-benzoquinone (550 mg, 2.5 mmol) in one portion. The solution was maintained at reflux 4 hours. After cooling on an ice bath, the solids were collected by filtration, suspended in MeOH (20 mL) and the product collected by filtration to give 280 mg (86%) of a yellow solid, mp>262–265° C. $^1$H NMR (DMSO-d$_6$, 300 z): δ3.4 (s, 3H), 4.2 (s, 2H), 7.35–7.5 (m, 4H), 7.6–7.8 (m, 2H), 8.3 (d, 1H), 8.95 (d, 1H), 11.1 (s, 1H), MS (ES$^-$) m/e 337 (M-1).

Example 7

Compound IV-4

Step 1: Intermediate IIc (Y=CH$_2$, R$^2$=H, R$^4$=5—Br, R$^6$=H).

This compound was prepared by the same general procedure as Examples Ia-IIa using indole (10.0 g, 85.3 mmol) and 5-bromo-1-indanone (19.0 g, 90 mmol) to give a crude alcohol intermediate Ic. The resulting crude alcohol as a dark oily residue, was dissolved in acetone (250 mL) followed by the addition of 2N HCL (25 mL), and water (50 mL). After stirring 2 h at room temperature the mixture was poured into water and extracted with EtOAc. The EtOAc was washed with water and brine, dried over MgSO$_4$, then concentrated at reduced pressure. The product was triturated with Et$_2$O and collected to give 8.7 g of intermediate IIc. $^1$H NMR (CDCl$_3$): δ3.56 (s, 2H), 6.68 (s, 1H), 6.90 (s, 1H), 7.12–7.25 (m, 3H), 7.40 (d, 1H), 7.52 (d, 1H), 7.66–7.74 (m, 3H), 8.26 (s, 1H). MS(ES$^+$): m/e 311 (m+1).

Step 2: Intermediate IIIc (Y=CH$_2$, R$^2$=H, R$^4$=5—Br, R$^6$=H)

This compound was prepared by the same general procedure as Example Ic using IIc (300 mg, 0.97 mmol) and maleimide (300 mg, 3.1 mmol) to give 210 mg (57%) of intermediate IIIc as a white solid. $^1$H NMR (DMSO-d$_6$): δ3.72–2.80 (m, 1H), 3.17–3.26 (m, 2H), 3.53 (m, 1H), 4.4 (m, 2H), 6.95–7.206 (m, 2H), 7.27 (d, 1H), 7.41–7.46 (m, 2H), 7.66–7.75 (m, 2H), 10.69 (s, 1H), 11.33 (s, 1H). MS(ES$^+$): m/e 407 (m$^+$).

Step 3: Compound IV-4

This compound was prepared by the same general procedure as compound IV-1 using IIIc (160 mg, 0.4 mmol) and 2,3-dichloro-5,6-dicyano-1,4-benzoquinone (228 mg, 1.0 mmol) to give 158 mg (100%) compound IV-4 as a yellow solid. $^1$H NMR (DMSO-d$_6$): δ4.34 (s, 2H), 7.36 (t, 1H), 7.62 (t, 1H), 7.73–7.82 (m, 2H), 7.98 (s, 1H), 8.52 (d, 1H), 8.93 (d, 1H), 11.18 (s, 1H), 12.18 (s, 1H). MS(ES$^-$): m/e 402 (m-1).

Example 8

Compound IV-5

Step 1: Intermediate I-id (Y=CH$_2$CH$_2$, R$^2$=R$^4$=H, R$^6$=H (2-(1-Hydroxy-1,2,3,4-tetrahydronaphthyl)indole))

This compound was prepared by the same general procedure as 1-ia using indole (15 g, 132 mmol) and 1-tetralone (20 g, 139 mmol) to yield 18 g (46%) of intermediate Id as a white solid. $^1$H NMR (CDCl$_3$): δ1.84–1.93 (m, 1H), 1.97–2.03 (m, 1H), 2.17–2.35 (m, 2H), 2.36 (s, 1H), 2.88–2.92 (, 2H), 6.10 (s, 1H), 7.07 (t, 1H), 7.13–7.19 (m 3H), 7.23–7.28 (m, 1H), 7.33–7.36 (m, 2H), 7.51 (d, 1H), 8.42 (s, 1H).

Step 2: Intermediate IId (Y=CH$_2$CH$_2$, R$^2$=R$^4$=H, R$^6$=H (2-[1-(3,4-Dihydro-naphthyl)]indole))

To a solution of alcohol I-id (15 g, 57 mmol) in acetone (150 mL) was added 2N HCl (3 mL). After stirring at room temperature for 1 h water was added to initiate precipitation of a solid The product was collected by filtration and dried to give 14 g (100%) of intermediate IId as a white solid. $^1$H NMR (CDCl$_3$): δ2.39–2.46 (m 2H), 2.82–2.87 (m, 2H), 6.38 (t, 1H), 6.59 (s, 1H), 7.09–7.25 (m, 5H), 7.34–7.40 (m, 2H), 7.61 (d, 1H), 8.11 (s, 1H). MS (ES$^+$) m/e 246 (M+1).

Step 3: Intermediate IIId (Y=CH$_2$CH$_2$, R$^2$=R$^4$=H, R$^6$=H)

A stirred mixture of diene IId (330 mg, 1.4 mmol) and maleimide was heated at 190° C. for 1 h. The mixture was cooled, dissolved in ethylacetate (50 mL) and washed repeatedly with hot water to remove excess maleimide. The EtOAc layer was dried (MgSO$_4$) concentrated and the resulting solid dried under vacuum at 80° C. to give 425 mg (89%) of IIId. MS (ES$^-$) m/e 341 (M-1).

Step 4: Compound V-5

To the imide intermediate IIId suspended in toluene (10 mL) was added 2,3-dichloro-5,6-dicyano-1,4-benzoquinone (160 mg, 0.7 mmol) in one portion followed by heating at 60–65° C. for 16 h. The suspension was concentrated and the product purified by column chromatography (silica gel, EtOAc:hexane; 1:1) to give 90 mg of a yellow solid. $^1$H NMR 67 2.81 (m, 2H), 3.16 (m, 2H), 7.27 (t, 1H), 7.40–7.54 (m, 4H), 7.67 (m, 1H), 8.12 (d, 1H), 8.88 (d, 1H), 11.10 (s, 1H), 11.85 (s, 1H). (DMSO-d$_{6, 300}$ MHz): δMS (ES$^-$) m/e 337 (M-1).

Example 9

Compound IV-6

Step 1: Intermediate I-ie. (Y=CH$_2$CH$_2$, R$^2$=5—OCH$_3$, R$^4$=H, R$^6$=H (2-(1-Hydroxy-1,2,3,4--tetrahydronaphthyl)-5-methoxyindole))

Intermediate I-ie was prepared by the same general procedure as I-ia using 5-methoxyindole (5.0 g, 34 mmol) and 1-tetralone (5.3 g, 34 mmol) to yield 6.2 g (62%) of intermediate I-ie as a white solid. $^1$H NMR (CDCl$_3$): δ1.84–1.90 (m, 1H), 1.96–2.03 (m, 1H), 2.16–2.33 (m, 2H), 2.36 (s, 1H), 2.90 (m, 2H), 3.80 (s, 3H), 6.03 (s, 1H), 6.82 (m, 1H), 6.97 (s, 1H), 7.13–7.25 (m, 4H), 7.32 (d, 1H), 8.31 (s, 1H).

Step 2: Intermediate IIe (Y=CH$_2$CH$_2$, R$^2$=5—OCH$_3$, R$^4$=H, R$^6$=H (2-[1-(3,4-Dihydronaphthyl)]-5-methoxyindole))

To a solution of alcohol I-ie (300 mg, 1.0 mmol) in acetone (10 mL) was added 2N HCl (1 mL). After stirring at room temperature for 1 h, water was added to precipitate the product which was collected by filtration and dried to give 200 mg (73%) of IIe as a red solid. $^1$H NMR (CDCl$_3$): δ2.41–2.45 (m, 2H), 2.81–2.86 (m, 2H), 3.86 (s, 3H), 6.35 (m, 1H), 6.52 (s, 1H), 6.83 (m, 1H), 7.08 (s, 1H), 7.12–7.25 (m, 4H), 7.39 (m, 1H), 8.01 (s, 1H). MS (ES$^+$) m/e 276 (M+1).

Step 3: Intermediate IIIe. (Y=CH$_2$CH$_2$, R$^2$=5—OCH$_3$, R$^4$=H, R$^6$=H)

This compound was prepared using the same general procedure as IIIa using IIe (150 mg, 0.54 mmol) and maleimide (105 mg, 1.1 mmol) to give 100 mg (50%) of IIIe as a white solid. MS (ES$^+$) m/e 373 (M+1).

Step 4: Compound IV-6

This compound was prepared using the same general procedure as compound IV-1 using imide IIIe from step 3 (80 mg, 0.22 mmol) and 2,3-dichloro-5,6-dicyano-1,4-benzoquinone (103 mg, 0.45 mmol) in dioxane (3 mL) to give 75 mg (95%). $^1$H NMR (DMSO-d$_6$): δ2.82 (m, 2H), 3.2 (m, 2H), 3.84 (s, 3H), 7.15 (m, 1H), 7.36–7.59 (m, 3H), 7.57 (d, 1H), 8.11 (d, 1H), 8.46 (s, 1H), 11.09 (s, 1H), 11.69 (s, 1H). MS (ES$^-$) m/e 367 (m–1).

Example 10

Compound IV-7

Step 1: Intermediate I-if (Y=CH$_2$CH$_2$, R$^2$=R$^4$=6—OCH$_3$, R$^6$=H (2-(1-Hydroxy-1,2,3,4-(6-methoxy)tetrahydronaphthyl)-2-indole))

Prepared by the same general procedure as intermediate I-ia using indole (7.0 g, 59.8 mmol) and 6-methoxy-1-tetralone (11.6 g g, 65.8 mmol) to yield 12.7 g (73%) of intermediate I-if as a white solid. $^1$H NMR (CDCl$_3$): δ1.83–2.01 (m, 2H), 2.16–2.25 (m, 2H), 2.86 (m, 2H), 3.80 (s, 3H), 6.12 (s, 1H), 6.67–6.73 (m, 2H), 7.04–7.17 (m, 2H), 7.23 (m, 1H), 7.34 (d, 1H), 7.50 (d, 1H), 8.40 (bs, 1H).

Step 2: Intermediate IIf (Y=CH$_2$CH$_2$, R$^2$=H, R$^4$=6—OCH$_3$, R$^6$=H (2-(6-Methoxy-(3,4-dihydronaphthyl))-2-indole))

This compound was prepared using the same general procedure as IIa using intermediate I-if (300 mg, 1.03 mmol) and 3 mL of 2N HCl to give 280 mg (100%) of If as a white foam. $^1$H NMR(CDCl$_3$): δ2.37–2.43 (m, 2H), 2.78–285 (m, 2H), 3.82 (s, 3H), 6.12 (s, 1H), 6.25 (m, 1H), 6.57 (s, 1H), 6.70 (d, 1H), 6.79 (s, 1H), 7.09–7.18 (m, 2H), 7.33–7.35 (m, 2H), 7.61 (d, 1H), 8.10 (bs, 1H). MS (ES$^+$) m/e 276 (M+1).

Step 3: Intermediate IIIf (Y=CH$_2$CH$_2$, R$^2$=H, R$^4$=6—OCH$_3$, R$^6$=H)

This compound was prepared using the same general procedure as IIIa using intermediate IIf (250 mg, 0.91 mmol) and maleimide (265 mg, 2.7 mmol) to give 225 mg (67%) of IIIf as a white foam. $^1$H NMR (CDCl$_3$): δ1.60–1.72 (m, 2H), 2.70–2.9 (m, 3H), 3.62 (m, 1H), 3.80 (s, 3H), 4.20 (m, 1H), 4.30 (m, 1H), 6.7 (s, 1H), 6.9 (m, 1H), 7.1–7.35 (m, 4H), 6.60 (s, 1H), 6.80 (s, 1H), 8.0 (d, 1H). MS (ES$^-$) m/e 371 (M–1).

Step 4: Compound IV-6

This compound was prepared using the same general procedure as compound IV-1 using imide IIIf from step 3 (35 mg, 0.094 mmol) and 2,3-dichloro-5,6-dicyano-1,4-benzoquinone (54 mg, 0.237 mmol) to give 31 mg (85%) of compound IV-6 as a yellow solid. $^1$H NMR (DMSO-d$_6$): δ2.80 (m, 2H), 3.2 (m, 2H), 3.83 (s, 3H), 7.03 (m, 2H), 7.27 (t, 1H), 7.50 (t, 1H), 7.66 (d, 1H), 8.06 (d, 1H), 8.87 (d, 1H), 11.05 (s, 1H), 11.76 (s, 1H). MS (ES$^+$) m/e 369 (M+1), 391 (M+23).

Example 11

Compound IV-8

Step 1: Intermediate I-ig (Y=CH$_2$CH$_2$, R$^2$=6—OCH$_3$, R$^4$=5-(2-ethoxy)ethoxy), R$^6$=H)

Prepared by the same general procedure as intermediate I-ia using 6-methoxyindole (1.5 g, 9.8 mmol) and 5-[(2-ethoxy)ethoxy]-1-tetralone (2.35 g, 10.0 mmol) to yield 1.8 g (47%) of intermediate I-ig as a white solid. $^1$H NMR (CDCl$_3$): δ1.23 (t, 3H), 1.83 (m, 1H), 1.94 (m, 1H), 2.10–2.32 (m, 4H), 2.74–2.83 (m, 2H), 3.64 (q, 2H), 3.83 (s, 3H), 4.15 (m, 2H), 6.02 (m, 1H), 6.72–6.80 (m, 3H), 7.00 (d, 1H), 7.12 (d, 1H), 7.25 (s, 1H), 7.36 (d, 1H), 8.41 (bs, 1H).

Step 2: Intermediate IIg (Y=CH$_2$CH$_2$, R$^2$=6—OCH$_3$, R$^4$=5-(2-ethoxy)ethoxy), R$^6$=H)

This compound was prepared using the same general procedure as IIa using intermediate Ig (200 mg, 0.52 mmol) and 2 mL of 2N HCl to give 175 mg (95%) of intermediate IIg as a white powder. $^1$H NMR (CDCl$_3$): δ1.25 (t, 3H), 2.32–2.40 (m, 2H), 2.85 (m, 2H), 3.65 (q, 2H), 3.81–3.85 (m, 2H), 3.82 (s, 3H), 4.15 (m, 2H), 6.33 (m, 1H), 6.49 (s, 1H), 6.76–686 (m, 3H), 7.02–7.15 (m, 2H), 7.45 (m, 1H), 7.97 (bs, 1H). MS(ES$^+$) m/e 364 (M+1).

Step 3: Intermediate IIIg. (Y=CH$_2$CH$_2$, R$^2$=6—OCH$_3$, R$^4$=5-(2-ethoxy)ethoxy), R$^6$=H)

This compound was prepared using the same general procedure as intermediate IIIa using example IIg (100 mg, 0.29 mmol) and maleimide (55 mg, 0.58 mmol) to give 55 mg (41%) of IIIg as a white foam. 1 MS (ES$^-$) m/e 459 (M–1).

Step 4: Compound IV-8

This compound was prepared using the same general procedure as compound IV-1 using imide IIIg from step 3 (50 mg, 0.11 mmol) and 2,3-dichloro-5,6-dicyano-1,4-benzoquinone (54 mg, 0.24 mmol) to give 45 mg (90%) of compound IV-8. $^1$H NMR (DMSO-d6): δ1.13 (t, 3H), 2.77 (m, 2H), 3.2 (m, 2H), 3.51 (q, 2H), 3.74 (m, 2H), 3.84 (s, 3H), 4.17 (m, 2H), 6.88 (m, 1H), 7.10–7.16 (m, 2H), 7.42 (m, 1H), 7.72 (m, 1H), 8.7 (d, 1H), 1.04 (s, 1H), 11.65 (s, 1H). MS (ES$^-$) m/e 455 (M–1).

Example 12

Compound IV-9

To compound IV-4 (50 mg, 0.15 mmol) in DMF (2 mL) was added NBS (31 mg, 0.18 mmol) followed by stirring at room temperature for 2 h. The solution was concentrated at reduced pressure. The residue was triturated with MeOH (3 mL) and the solid collected and washed with MeOH to give 55 mg (89%) of compound IV-9 as a yellow solid. mp>300°

C.; $^1$H NMR (DMSO-d$_6$, 300 M): δ2.82 (m, 2H), 3.12 (m, 2H), 7.43–7.53 (m, 4H), 7.68 (s, 1H), 8.14 (d, 1H), 9.06 (s, 1H), 11.24 (s, 1H), 12.05 (s, 1H). MS (ES-) m/e 416 (M−1).

Example 13

Compound X-2

Step 1: A mixture of intermediate II-d (2-[1-(3,4-dihydronaphthyl)]indole) (1.0 g, 4.1 mmol) and ethyl cis-β-cyanoacrylate (2.0 g, 16.0 mmol) was heated at 190° C. with stirring for 1 h. While cooling to room temperature, MeOH (10 mL) was added and stirring was continued for 0.5 h. The solid which separated was collected to give 1.2 g of (79%) as a white solid. The solid was a 1:1 mixture of 2 isomers and showed a mp>300° C., MS (ES$^+$) m/e 371 (M+1). This intermediate was used directly in the next step.

Step 2: To the mixture of isomers from step 1 (500 mg, 1.35 mmol) in toluene (50 mL) was added solid 2,3-dichloro-5,6-dicyano-1,4-benzoquinone (678 mg, 3.0 mmol) in one portion. The mixture was heated to 60–65° C. for 18 h. The reaction was concentrated at reduced pressure. The resulting material was dissolved in EtOAc (75 mL), washed with 2N NaOH (2×50 mL), water (2×50 mL), saturated NaCl solution (2×50 mL), dried (MgSO$_4$) and concentrated to give 480 mg (97%) of the product as a 1:1 mixture of 3-cyano and 4-cyano isomers. This intermediate was used directly in the next step.

Step 3: A 1:1 mixture of isomers (450 mg, 1.2 mmol) from step 3 in DMF:MeOH (1:1, 10 mL) and 1 spatula full of RaNi was hydrogenated at 55 psi for 18 h. The catalyst was removed by filtration and the solvent removed at reduced pressure. The solid was triturated with ether to give 350 mg (90%) of a 1:1 mixture of lactam isomers IX-2: X-2.

Step 4: Compound X-2

To the lactam isomers from step 3 (300 mg, 0.93 mmol) in DMF (10 mL) was added triethylamine (190 mg, 0.25 mL) and t-Butyldimethylsilyl chloride (285 mg, 1.9 mmol). The solution was stirred 1 h at room temperature at which time TLC (silica gel, ether:hexane; 1:1) showed the reaction to be ca 50% complete. The DMF was removed at reduced pressure and the residue dissolved in EtOAc washed with water and NaCl solution and dried (MgSO$_4$). The solvent was removed and the resulting solid triturated with ether. Compound X-2 was collected and dried; mp>300° C. $^1$H NMR (DMSO-d$_6$, 300 MHz): δ2.8 (b, 4H), 4.5 (s, 2H), 7.21 (t, 1H), 7.37–7.51 (m, 4H), 7.65 (d, J=8 Hz, 1H), 8.23 (d, J=7.6 Hz, 1H), 8.63 (s, 1H), 9.14 (d, J=7.7 Hz), 11.48 (s, 1H). MS (ES-) m/e 371 (M+1).

Example 14

Compound IX-2

The ether solution from example 13 step 4 was concentrated and THF added followed by TBAF (2 mL, 1 M in THF). The solution was stirring at room temperature for 4 h, after which the solvent was removed and the resulting solid triturated with water, collected. The product was washed with ether and dried (60° C., 1 mm) to give compound IX-2 as a white solid. mp>300° C. $^1$H NMR (DMSO-d$_6$, 300 MHz): δ2.77–2.81 (m, 2H), 3.49–3.52 (m, 2H), 4.83 (s, 2H), 7.23–7.36 (m, 2H), 7.42–7.51 (m, 3H), 7.70 (d, 1H), 7.78 (d, 1H), 8.15 (d, 1H), 8.46 (s, 1H), 11.61 (s, 1H). MS (ES-) m/e 371 (M+1).

Example 15

Compound XIII

Step 1: Intermediate XI (R$^2$=R$^4$=R$^6$=H)

To a solution of 7-azaindole (5.2 g, 44 mmol) in dry THF (120 mL) cooled to −78° C. under a nitrogen atmosphere was add BuLi (46.2 mmol, 18.5 mL of 2.5 M solution in hexanes) slowly. Following stirring for 30 min, CO$_2$(g) was passed through the solution for 10 min after which the clear solution was concentrated to ca two-thirds volume at reduced pressure. The volume of THF was brought to about 125 mL and cooled to −78° C. t-BuLi (44 mmol, 26 mL of 1.7 M solution in hexanes) was added slowly while maintaining the temperature below 68° C. followed by stirring for 2 h at −78° C. To this orange solution was added 1-tetralone (6.8 g, 46.2 mmol) in THF (10 mL) dropwise. The mixture stirred for 1.5 h, then poured into 2N HCl (150 mL) extracted with EtOAc (1×150 mL) and the HCl layer stirred for 18 h. The HCl solution was made basic with 2N NaOH and the precipitate that formed was collected to give 6.7 g (63%) of intermediate XIII. $^1$H NMR (DMSO-d$_6$): δ2.35 (m, 2H), 2.74 (m, 2H), 6.41 (s, 1H), 6.52 (m, 1H), 7.02 (m, 1H), 7.17–7.24 (m, 3H), 7.35 (m, 1H), 7.88 (m, 1H), 8.15 (m, 1H), 11.76 (s, 1H). MS (ES$^+$) m/e 247 (M+1).

Step 2: Intermediate XII (R$^2$=R$^4$=R$^6$=H)

A mixture of intermediate XI (100 mg, 0.41 mmol) and maleimide 79 mg, 0.81 mmol) in xylenes (8 mL) was maintained at reflux 14 h. The reaction was cooled to room temperature and the solid which separated was collected, washed with ether and dried to give 90 mg (64%) of compound XII as a tan solid; MS (ES$^-$) m/e 341 (M−1).

Step 3: Compound XIII

To a suspension of XII (35 mg, 0.1 mmol) in dioxane (3.5 mL) was added solid DDQ (45 mg, 0.2 mmol). The reaction was stirred at room temperature for 12 h. Methanol (5 mL) was added and the mixture cooled in a freezer. A light tan precipitate was collected and dried to give 20 mg (58%) of compound XIII. $^1$H NMR (DMSO-d$_6$): δ2.88 (m, 2H), 3.2 (m, 2H), 7.39–7.48 (m, 4H), 8.17 (d, 1H), 8.62 (d, 1H), 9.14 (d, 1H), 11.25 (s, 1H), 12.48 (s, 1H). MS(ES$^-$): m/e 338 (m−1).

Example 16

Compound III-2

Step 1: Intermediate IIg (Y=S, R$^2$=R$^4$=R$^6$=H (2-(3-Benzothieno)indole))

To a solution of 1-carboxy-2-tributylstannylindole (9.5 g, 21.0 mmol) and 3-bromobenzothiaphene (3.0 g, 14.1 mmol) in EtOH (75 mL) was added dichlorobis (bistriphenylphosphine) palladium(II) (771 mg, 1.1 mmol). The mixture was stirred at reflux under nitrogen for 16 h, cooled to room temperature and concentrated at reduced pressure. The resulting dark oil was rinsed with an ether-hexane (1:1) solution and decanted (2×) leaving a brown solid. This solid was recrystallized from hot MeOH to give 3.2 g (65%) of a tan solid. $^1$H NMR (DMSO-d$_6$): δ6.94 (s, 1H), 7.04 (t, 1H), 7.15 (t, 1H), 7.43–7.62 (m, 4H), 8.04 (s, 1H), 8.09 (d, 1H), 8.29 (d, 1H), 11.55 (s, 1H). MS(ES$^+$): m/e 250 (m+1).

Step 2: Compound E-2

2-(3-Benzothieno)indole (IIg, step 1) (100 mg, 0.4 mmol), maleimide (77 mg, 0.8 mmol) and trifluoroacetic acid (ca 10 drops) in toluene (10 mL) was maintained at reflux 12 h. The reaction was cooled to room temperature and the solid collected, and washed with toluene and ether to give 75 mg (54%) of compound E1-2 as a tan solid. $^1$H NMR (DMSO-d$_6$): δ3.73 (m, 1H), 4.47(m, 1H), 4.90 (m, 1H), 4.96 (m, 1H), 6.96–7.06 (m, 2H), 7.17–7.30 (m, 3H), 7.68 (m, 1H), 7.77 (m, 1H), 10.45 (s, 1H), 11.38 (s, 1H). MS(ES⁻): m/e 345 (m–1).

Example 17

Compound IV-10

To a suspension of compound III-2 (IIIg) (30 mg, 0.09 mmol) in dioxane (4 mL) was added solid DDQ (60 mg, 0.26 mmol). After heating at 65° C. for 12 h, the mixture was concentrated, the product triturated with methanol, collected and dried to give 24 mg (78%) of IV-10. ¹H NMR(DMSO-d₆): δ7.38 (t, 1H), 7.56–7.82 (m, 4H, 8.23 (d, 1H), 8.92 (d, 1H), 9.00 (d, 1H), 11.32 (s, 1H), 12.37 (s, 1H). MS(ES⁻): m/e 341 (m–1).

Example 18

Compound XVII

Step 1: Intermediate XIV (R²=H)

This compound was prepared by the same general procedure as intermediate 1-ia starting with indole (3.5 g, 29.9 mmol) and 4-keto-4,5,6,7-tetrahydrothianaphthlene (5.0 g, 32.9 mmol) to give 6.5 g (81%) of XIV as a white solid. ¹H NMR (CDCl₃): δ1.93–2.09 (m, 2H), 2.16–2.24 (m, 2H), 2.33 (s, 1H), 2.86–2.93 (m, 2H), 6.16 (s, 1H), 6.87 (d, 1H), 7.05–7.18 (m, 3H), 7.35 (d, 1H), 7.52 (d, 1H), 8.44 (s, 1H).

Step 2. Intermediate XV (R²=H)

This compound was prepared by the same general procedure as IIa using XIV (200 mg, 0.74 mmol) to give the diene XV as a white unstable glass. ¹H NMR (CDCl₃): δ2.52–2.59 (m, 2H), 2.89–295 (m, 2H), 6.13 (m, 1H), 6.61 (s, 1H), 7.08–7.22 (m, 4H), 7.35 (d, 1H), 7.60 (d, 1H), 8.14 (s, 1H). MS (ES⁺) m/e 252 (M+1).

Step 3: Compound XVI (R²=H)

This compound was prepared by the same general procedure as ia using diene XV (250 mg, 1.0 mmol) and maleimide (194 mg, 2.0 mmol) to give 225 mg (66%) from MeOH-ether. MS (ES⁺) m/e 347 (M–1).

Step 4: Compound XVII

A mixture of XVI (70 mg, 0.2 mmol) and DDQ (136 mg, 0.6 mmol) was heated at 65° C. for 40 h. The mixture was concentrated and the product (Rf 0.4) isolated by column chromatography (silica gel, EtOAc: hex; 2:1) as a yellow solid. ¹H NMR (DMSO-d₆, 300 MHz): δ7.43 (t, 1H), 7.63 (t, 1H), 7.96 (d, 1H), 8.33 (d, 1H), 8.43 (d, 1H), 8.96 (d, 1H), 9.07 (d, 1H), 9.13 (d, 1H), 11.25 (s, 1H), 12.21 (s, 1H). MS (ES⁺) m/e 341 (M–1).

Example 19

Compound IV-11

Step 1: Intermediate I-ih (Y=CH₂O, R²=R⁴=R⁶=H)

This compound was prepared by the same general procedure as I-ia using indole (7.0 g, 35 mmol) and 4-chromanone (9.74 g, 65.8 mmol) to give 12.5 g (79%) as a crude oil. A sample was recrystallized from ether-hexane. ¹H NMR (CDCl₃): δ2.30–2.49 (m, s, 3H), 4.26–4.43 (m, 2H), 6.25 (s, 1H), 6.86–6.93 (m, 2H), 7.07–7.27 (m, 3H), 7.35 (d, 1H), 7.54 (d, 1H), 8.39 (s, 1H).

Step 2: Intermediate IIh (Y=CH₂O, R²=R⁴=R⁶=H)

The oil from step 1 was dissolved in acetone (125 mL) and added 2N HCl (20 mL) followed by stirring 1 h at rt. The precipitate was collected washed with water and dried to give 11 g (76% 2 steps). ¹H NMR (CDCl₃): δ4.82 (d, 2H), 6.06 (m, 1H), 6.64 (s, 1H), 6.93–6.97 (m, 2H), 7.11–7.25 (m, 3H), 7.36–7.43 (m, 2H), 7.62 (d, 1H), 8.13 (s, 1H). MS (ES⁺) m/e 248 (m+1).

Step 3: Intermediate IIIh (Y=CH₂O, R²=R⁴=R⁶=H)

This compound was prepared by the same general procedure as IIIa using diene IIh (300 mg, 1.2 mmol) and maleimide (235 mg, 2.4 mmol). After cooling to room temperature the residue was dissolved in EtOAc (50 mL) and washed with hot water (3×50 mL) dried (MgSO₄) and concentrated to give a yellow solid, MS (ES⁻) m/e 343 (M–1).

Step 4: Compound IV-11

The product from step 3 (IIh) in toluene (10 mL) was added DDQ (684 mg, 3.0 mmol) and heated at 65° C. for 16 h. The mixture was cooled to room temperature and the solid precipitate collected, washed with MeOH and dried to give 290 mg (71% 2 steps) of crude solid. The product was purified by column chromatography (silica gel, toluene: THF; 10%-30% THF). ¹H NMR (DMSO-d₆,300 MHz): δ7.24 (m, 1H), 7.33–7-38 (m, 2H), 7.59 (m, 1H), 7.62 (m, 2H), 7.80 (m, 1H), 8.38 (d, 1H), 8.98 (d, 1H), 11.30 (s, 1H), 12.08 (s, 1H). MS (ES⁺) m/e 339 (M–1).

Example 20

Compound IX-3

Step 1: A mixture of diene IIh (880 mg, 3.6 mmol) and ethyl cis-β-cyanoacrylate (1.8 g, 14.4 mmol) was heated at 190° C. with stirring for 1 h. Methanol (15 mL) was added while hot, followed by stirring at room temperature for 3 h. The solid which separated was collected and dried under vacuum to give 550 mg (41%) of the 4-CN isomer (intermediate V, Y=CH₂O, R²=R⁴=H) as a yellow solid ¹H NMR (DMSO-d₆, 300 MHz): δ1.33 (t, 3H), 3.11–3.17 (m, 1H), 3.81–3.84 (m, 1H), 4.00–4.08 (m, 1H), 4.31–4.41 (m, 4H), 4.77 (d, 1H), 6.87 (d, 1H), 7.04–7.15 (m, 3H), 7.23 (t, 1H), 7.42 (d, 1H), 7.57 (d, 1H), 7.64 (d, 1H), 10.69 (s, 1H). MS (ES⁺) m/e 373 (M+1). The MeOH layer was reduced under pressure to about half volume and ether was added to initiate precipitation. After cooling at freezer temperature overnight, 325 mg of a solid was isolated as a 1:1 mixture of isomers V (Y=CH₂O, R²=R⁴=H) and VI (Y=CH₂O, R²=R⁴=H) by ¹H NMR.

Step 2:1 The 4-CN isomer from step 1 (500 mg, 1.3 mmol) and DDQ (740 mg, 3.3 mmol) in toluene was heated for 18 h at 60° C. The solution was concentrated and the residue dissolved in EtOAc, washed with 2N NaOH (2×), water, brine and dried (MgSO₄). After concentrating the solvent, the product was triturated with MeOH to give 320 mg (67%). ¹H NMR (DMSO-d₆, 300 MHz): δ1.43 (t, 3H), 4.48 (q, 2H), 5.37 (s, 2H), 7.20 (d, 1H), 7.36–7.49)m, 3H), 7.65 (t, 1H), 7.81 (d, 1H), 8.25 (d, 1H), 8.58 (d, 1H), 12.12 (s, 1H). MS (ES⁺) m/e 369 (M+1).

Step 3: Compound IX-3

The cyano-ester product from step 2 (300 mg, 0.82 mmol) in DMF:MeOH (20 mL, 1:1) was added a spatula full of RaNi and hydrogenated at 55 psi on a Par apparatus for 14 h. The solution was filter through celite and concentrated. The product was recrystallized from MeOH to give 200 mg (75%) as a white solid. ¹H NMR (DMSO-d₆, 300 MHz): δ4.90 (s, 2H), 5.75 (s, 2H), 7.15 (d, 1H), 7.29–7.38 (m, 3H), 7.52 (t, 1H), 7.75 (d, 1H), 8.02 (d, 1H), 8.22 (d, 1H), 8.62 (s, 1H), 11.73 (s, 1H). MS (ES⁺) m/e 326 (M⁺).

Example 21

Compound X-3

The mixture of isomers from step 1 in Example 20 (330 mg, 0.9 mmol) was oxidized using DDQ (607 mg, 2.7 mmol) using the same general procedure as example 20, step 3, to give 300 mg (90%). The isomers were dissolved in DMF:MeOH (1:1, 30 mL) and hydrogenated by the same general procedure as example 20 step 4 to give 175 mg. Compound X-3 was obtained from MeOH. $^1$H NMR (DMSO-$d_6$, 300 MHz): δ4.58 (s, 2H), 5.25 (s, 2H), 7.15–7.50 (m, 6H), 7.70 (d, 1H), 8.30 (d, 1H), 8.60 (s, 1H), 9.20 (d, 1H), 11.60 (s, 1H). MS (ES$^+$) m/e 326 (M$^+$).

Example 22

Compound X-4

Step 1: Intermediate XVIII ($R^2=R^4=H$)

NaH (325 mg, 8.2 mmol, 60% oil dispersion) was added to a solution of diene IId (1.0 g, 4.1 mmol) in dry DMF (40 mL). After stirring at room temperature 1 h., mesyl 2-benzyloxyethanol was added (1.9 g, 8.2 mmol). The reaction was heated to 70° C. in an oil bath for 18 h, cooled to room temperature and poured into water (100 mL). The product was extracted with EtOAc (2×100 mL), followed by washing with water (2×100 mL) sodium chloride solution (2×100 mL) and dried (MgSO$_4$). The solution was concentrated at reduced pressure and the resulting product was triturated with ether: hexane solution (1:1) to give 1.45 g (95%) of a tan solid. $^1$H NMR (CDCl$_3$,): δ2.38 (m, 2H), 2.86 (t, 2H), 3.59 (t, 2H), 4.12 (t, 2H), 4.31 (s, 2H), 6.20 (t, 1H), 6.47 (s, 1H), 6.74 (d, 1H), 7.02 (t, 1H), 7.10–7.25 (m, 9H), 7.38 (d, 1H), 7.62 (d, 1H). MS (ES$^+$) m/e 380 (m+1).

Step 2: Intermediate XIX b($R^2=R^4=H$)

Oxalyl chloride (0.15 mL, 1.7 mmol) was added slowly to the product from step 1 (650 mg, 1.7 mmol) in CH$_2$Cl$_2$ (25 mL) at ice bath temperature. The solution was stirred for 0.5 h, then anhydrous MeOH (2 mL) was added followed by stirring at room temperature for 0.5 h. The solution was concentrated, dissolved in EtOAc and washed with 2N NaOH (2×), water (2×), sodium chloride solution (2×) dried (MgSO$_4$) and concentrated to a dark oil. Purification by column chromatography (silica gel, EtOAc: hex; 1:1) gave 0.5 g (63%) as an oil. $^1$H NMR (CDCl$_3$,): δ2.35–2.42 (m, 2H), 2.83–2.89 (m, 2H), 3.23 (s, 3H), 3.51–3.68 (m, 2H), 3.96–4.06 (m, 1H), 4.10–4.24 (m, 1H), 4.31 (s, 2H), 6.11 (m, 1H), 6.70 (d, 1H), 7.04–7.09 (m, 2H), 7.18 (m, 2H), 7.24 (m, 4H), 7.32–7.39 (m, 2H), 7.40 (m, 1H), 8.45 (m, 1H). MS (ES$^+$) m/e 466 (m+1).

Step 3: Intermediate XX ($R^2=R^4=H$)

A mixture of diethyl cyanomethylphosphonate, intermediate XIX (160 mg, 0.34 mmol), and Na$_2$CO$_3$ (43 mg, 0.41 mmol) in dry THF (25 mL) was stirred at reflux for 4 h. The reaction was cooled to room temperature and concentrated. The residue was dissolved in EtOAc (50 mL), washed 2× with 2N NaOH, water, brine, dried (MgSO$_4$) and concentrated to give 150 mg (90%/o) as a yellowish solid. $^1$H NMR (CDCl$_3$,): δ2.40 (m, 2H), 2.80–2.87 (m, 2H), 3.20 (s, 3H), 3.5–3.65 (m, 2H), 2.95–4.05 (m, 1H), 4.15–4.25 (m, 1H), 4.3 (s, 2H), 5.95 (s, 1H), 6.05 (m, 1H), 6.65 (d, 1H), 7.05–7.1 (m, 2H), 7.18 (m, 2H), 7.2–7.4 (m, 6H), 7.45 (m, 1H), 7.7 (m, 1H). IR cm$^{-1}$ 2240 (CN). MS (ES$^+$) m/e 489 (m+1).

Step 4: Intermediate XXI ($R^2=R^4=H$)

Intermediate XX (500 mg, 1.1 mmol), chloronil (270 mg, 1.2 mmol) and palladium acetate (240 mg, 1.1 mmol) in dichlorobenzene (40 ml) was stirred at reflux under nitrogen 24 h. The solution was concentrated, the reside dissolved in EtOAc and extracted with 2M Na$_2$CO$_3$ solution (3×) and dried (MgSO4). The product was purified by column chromatography (Rf 0.5, silica gel, EtOAc: hexane; 1:1). MS (ES$^+$) m/e 487 (m+1), 509 (m+23).

Step 5: Compound X-4

The product from step 4 in DMF-MeOH (10 mL+5 mL) was added a spatula full of RaNi, and hydrogenated on a Parr Apparatus for 14 h. The solution was filtered to remove catalyst then concentrated at reduced pressure. The residue was dissolved in DMF-MeOH (1:1, 15 mL) and Pd(OH)$_2$ (50 mg, 20%/C) was added, and hydrogenated on a Parr Apparatus for 12 h. The solution was filtered and concentrated at reduced pressure. The product was triturated with Et$_2$O-hexane and collected to give 1X-4. $^1$H NMR (CDCl$_3$,): δ2.95–3.0 (m, 4H), 4.20 (m, 1H), 4.44.5 (b, 6H), 7.21 (m, 1H), 7.28–7.46(m, 4H), 7.57 (d, 1H), 7.66 (d, 1H), 8.60 (s, 1H), 9.18 (d, 1H). MS (ES$^+$) m/e 369 (m+1), 391 (m+23).

Additional compounds IV-12 to IV-44, IX-4, IX-5, X-5, and X-6, and were prepared by the methods consistent with Examples 1 to 22. These compounds as well as those set forth in the foregoing examples may be further understood by reference to Tables 1–4, presented for illustrative purposes, wherein each entry corresponds to the accompanying structure.

TABLE 1

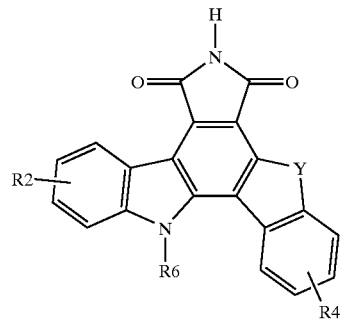

| Compound | Y | R2 | R4 | R6 |
| --- | --- | --- | --- | --- |
| IV-1 | CH$_2$ | H | H | H |
| IV-2 | C=O | H | H | H |
| IV-3 | CH$_2$ | H | H | CH$_3$ |
| IV-4 | CH$_2$ | H | 10-Br | H |
| IV-5 | CH$_2$CH$_2$ | H | H | H |
| IV-6 | CH$_2$CH$_2$ | 3-OCH$_3$ | H | H |

TABLE 1-continued

[Structure: fused ring system with R2 on left benzene, R4 on right benzene, R6 on indole N, Y bridging position, and maleimide top]

| Compound | Y | R2 | R4 | R6 |
|---|---|---|---|---|
| IV-7 | CH$_2$CH$_2$ | H | 11-OCH$_3$ | H |
| IV-8 | CH$_2$CH$_2$ | 2-OCH$_3$ | 10-O(CH$_2$)$_2$—OCH$_2$CH$_3$ | H |
| IV-9 | CH$_2$CH$_2$ | 3-Br | H | H |
| IV-10 | S | H | H | H |
| IV-11 | CH$_2$O | H | H | H |
| IV-12 | CHCH$_2$OCH$_3$ | H | H | H |
| IV-13 | CH[CHOH(3-Pyr)] | H | H | H |
| IV-14 | CH[CHOH(CH$_3$)] | H | H | H |
| IV-15 | CHCH$_2$OH | H | H | H |
| IV-16 | CH(2-thieno) | H | H | H |
| IV-17 | CH[CH$_2$OCH$_2$CH$_2$OCH$_3$] | H | H | H |
| IV-18 | CH[CHOH(4-Pyr)] | H | H | H |
| IV-19 | CH$_2$CH$_2$ | H | H | CH$_2$CH$_2$CN |
| IV-20 | CH$_2$CH$_2$ | H | H | CH$_2$CH$_2$CH$_2$CN |
| IV-21 | CH$_2$CH$_2$ | H | H | CH$_2$CH$_2$CO$_2$Et |
| IV-22 | CH$_2$CH$_2$ | H | H | CH$_2$CH$_2$CO$_2$H |
| IV-23 | CH$_2$CH$_2$ | H | H | CH$_2$CH$_2$CH$_2$NH$_2$ |
| IV-24 | CH$_2$CH$_2$ | H | H | CH$_2$CH$_2$CH$_2$NHSO$_2$CH$_3$ |
| IV-25 | CH$_2$CH$_2$ | H | H | CH$_2$CH$_2$CH$_2$NHCOCH$_3$ |
| IV-26 | CH$_2$CH$_2$ | H | H | CH$_2$CH$_2$CH$_2$NHCSNHCH$_3$ |
| IV-27 | CH$_2$CH$_2$ | H | H | CH$_2$CH$_2$CH$_2$NHCONHPh |
| IV-28 | CH$_2$CH$_2$ | H | H | pentyl-NHC(O)-(2,6-dichlorophenyl) |
| IV-29 | CH$_2$CH$_2$ | H | H | butyl-NHC(O)-proline-N-boc |
| IV-30 | CH$_2$CH$_2$ | H | H | butyl-NHC(O)-proline-NH |
| IV-31 | CH$_2$CH$_2$ | H | H | butyl-NHC(O)-proline-N-SO$_2$CH$_3$ |
| IV-32 | CH$_2$CH$_2$ | 3-CN | H | H |
| IV-33 | CH$_2$CH$_2$ | 3-CH$_2$NH$_2$ | H | H |
| IV-34 | CH$_2$CH$_2$ | 3-CH$_2$NHSO$_2$CH$_3$ | H | H |
| IV-35 | CH$_2$CH$_2$ | 3-CH$_2$NHCSNH—CH$_3$ | H | H |
| IV-36 | CH$_2$CH$_2$ | 3-CH=CHCO$_2$$^t$Bu | H | H |
| IV-37 | CH$_2$CH$_2$ | 3-CH=CHCO$_2$H | H | H |
| IV-38 | CH$_2$CH$_2$ | 3-CH$_2$CH$_2$CO$_2$$^t$Bu | H | H |

TABLE 1-continued
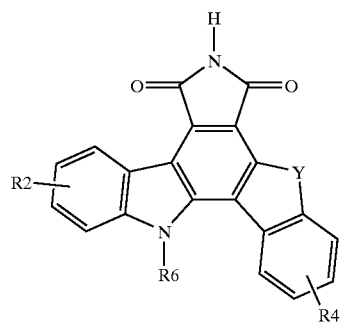
| Compound | Y | R2 | R4 | R6 |
|---|---|---|---|---|
| IV-39 | CH₂CH₂ | 3-CH=CH(2-Pyr) | H | H |
| IV-40 | CH₂CH₂ | 3-CH₂CH₂CO₂H | H | H |
| IV-41 | CH₂CH₂ | H | H | (CH₂)₃OBn |
| IV-42 | CH₂CH₂ | H | H | (CH₂)₃OH |
| IV-43 | CH₂CH₂ | 3-CH=CHCN | H | H |
| IV-44 | CH₂CH₂ | 3-CN | H | H |
TABLE 2
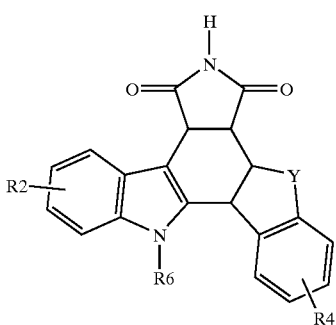
| Compound | Y | R2 | R4 | R6 |
|---|---|---|---|---|
| III-1 | CH₂ | H | H | CH₃ |
| III-2 | S | H | H | H |
TABLE 3
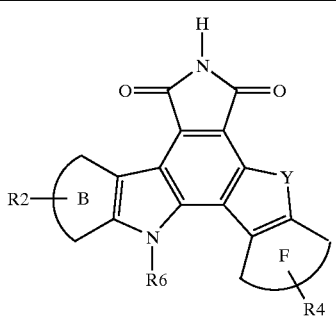
| Compound | Y | B-R2 | F-R4 | R6 |
|---|---|---|---|---|
| XIII | CH₂CH₂ | 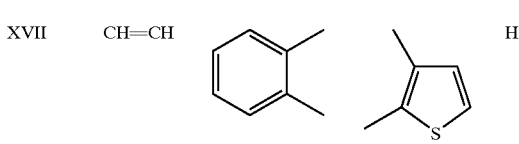 | | H |
TABLE 3-continued
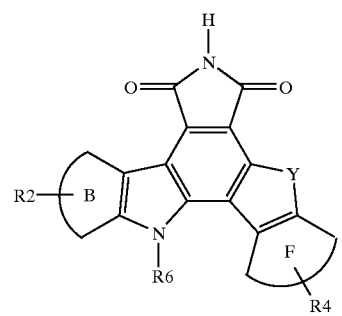
| Compound | Y | B-R2 | F-R4 | R6 |
|---|---|---|---|---|
| XVII | CH=CH | (o-xylyl) | (2,3-dimethylthienyl) | H |

TABLE 4

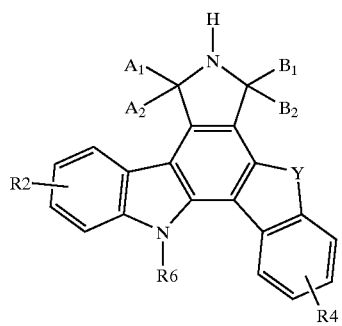

| Compound | A1,A2 | B1,B2 | Y | R2 | R4 | R6 |
|---|---|---|---|---|---|---|
| IX-1 | H,H | =O | $CH_2$ | H | H | H |
| IX-2 | H,H | =O | $CH_2CH_2$ | H | H | H |
| IX-3 | H,H | =O | $CH_2O$ | H | H | H |
| X-1 | =O | H,H | $CH_2$ | H | H | H |
| X-2 | =O | H,H | $CH_2CH_2$ | H | H | H |
| X-3 | =O | H,H | $CH_2O$ | H | H | H |
| X-4 | =O | H,H | $CH_2$ | H | H | $CH_2CH_2OH$ |
| IX-4 | H,H | =O | $CH_2CH_2$ | H | H | $CONHCH_2CH_2OH$ |
| X-5 | =O | H,H | $CH_2$ | 3-Br | H | H |
| X-6 | =O | H,H | C=O | H | H | H |
| IX-5 | H,H | =O | $CH_2$ | 3-Br | H | H |
| IX-6/X-7(40:60) | H,H/=O | =O/H,H | $CH_2CH_2$ | H | H | $CH_2$(2-Pyr) |

Utility

The isomeric fused pyrrolocarbazoles and isoindolones of the present invention are useful, inter alia, as therapeutic agents. Particularly, the compounds are useful for kinase inhibition. The isomeric fused pyrrolocarbazoles and isoindolones have been shown to inhibit, for example, one or more of trk kinase, platelet derived growth factor receptor (PDGFR) kinase, vascular endothelial growth factor receptor (VEGFR) kinase, or NGF-stimulated trk phosphorylation.

The properties of the compounds of the present invention are beneficial in therapeutic settings. The activities of the fused pyrrolocarbazoles and isoindolones toward certain enzymes can be exploited to combat the deleterious consequences of these enzymes. Particularly, inhibition of the Vascular Endothelial Growth Factor Receptor (VEGFR) implies utility in, for example, diseases where angiogenesis plays important roles, such as cancer of solid tumors, endometriosis, diabetic retinopathy, psoriasis, hemangioblastoma, as well as other ocular diseases and cancers. Inhibition of trk implies utility in, for example, diseases of the prostate such as prostate cancer and benign prostate hyperplasia, and treatment of inflammatory pain. Inhibition of the Platelet Derived Growth Factor Receptor (PDGFR) implies utility in, for example, various forms of neoplasia, rheumatoid arthritis, pulmonary fibrosis, myelofibrosis, abnormal wound healing, diseases with cardiovascular end points, such as atherosclerosis, restenosis, post-angioplasty restenosis, and the like.

The activities of isomeric fused pyrrolocarbazoles and isoindolones have also been shown to have positive effects on the function and survival of trophic factor responsive cells by promoting the survival of neurons. With respect to the survival of a cholinergic neuron, for example, the compound may preserve the survival of a cholinergic neuronal population at risk of dying (due to, e.g., injury, a disease condition, a degenerative condition or natural progression) when compared to a cholinergic neuronal population not presented with such compound, if the treated population has a comparatively greater period of functionality than the non-treated population.

A variety of neurological disorders are characterized by neuronal cells which are dying, injured, functionally compromised, undergoing axonal degeneration, at risk of dying, etc. These disorders include, but are not limited to, Alzheimer's disease; motor neuron disorders (e.g. amyotrophic lateral sclerosis); Parkinson's disease; cerebrovascular disorders (e.g., stroke, ischaemia); Huntington's disease; AIDS dementia; epilepsy; multiple sclerosis; peripheral neuropathies (e.g., those affecting DRG neurons in chemotherapy-associated peripheral neuropathy) including diabetic neuropathy; disorders induced by excitatory amino acids; and disorders associated with concussive or penetrating injuries of the brain or spinal cord.

The compounds are not only useful for enhancing trophic factor-induced activities of trophic responsive cells, e.g., cholinergic neurons, but also may function as survival promoting agents for other neuronal cell types, e.g., dopaminergic or glutamatergic. Growth factor may regulate survival of neurons by signaling cascades downstream of the small GTP binding proteins ras, rac, and cdc42 (Denhardt, D. T., Biochem. J., 1996, 318, 729). Specifically, activation of ras leads to phosphorylation and activation of extracellular receptor-activated kinase (ERK), which has been linked to biological growth and differentiation processes. Stimulation of rac/cdc42 leads to an increase in activation of JNK and p38, responses that are associated with stress, apoptosis, and inflammation. Although growth factor responses are primarily via the ERK pathway, affecting these latter processes may lead to alternative mechanisms of neuronal survival which may mimic growth factor enhancing survival properties (Xia et al., Science, 1995, 270, 1326). The compounds may also function as survival promoting agents for neuronal and non-neuronal cells by mechanisms related to, but also distinct from, growth factor mediated survival, for example, inhibition of the JNK and p38 MAPK pathways which may lead to survival by inhibition of apoptotic cell death processes.

The present compounds are also useful in the treatment of disorders associated with decreased ChAT activity or the death, injury to spinal cord motoneurons, and also have utility in, for example, diseases associated with apoptotic cell death of the central and peripheral nervous system, immune system and in inflammatory diseases. ChAT catalyzes the synthesis of the neurotransmitter acetylcholine, and it is considered an enzymatic marker for a functional cholinergic neuron. A functional neuron is also capable of survival. Neuron survival is assayed by quantitation of the specific uptake and enzymatic conversion of a dye (e.g., calcein AM) by living neurons. The compounds described herein may also find utility in the treatment of disease states involving malignant cell proliferation, such as many cancers.

Because of their varied utilities, the properties of isomeric fused pyrrolocarbazoles and isoindolones may be exploited in other settings, such as research. For example, the compounds can be used in the development of in vitro models of neuronal cell survival, function, identification, or for the screening of other synthetic compounds which have activities similar to that of the of isomeric fused pyrrolocarbazole and isoindolone compounds. Thus, the compounds provided by this invention are useful as standard or reference compounds for use in tests or assays for determining the activity of an agent in a pharmaceutical research program.

The compounds can also be utilized to investigate, define and determine molecular targets associated with functional responses. For example, by radiolabelling an isomeric fused pyrrolocarbazole or isoindolone compound associated with a specific cellular function (e.g., mitogenesis), the target entity to which the derivative binds can be identified, isolated, and purified for characterization. By way of further illustration, compounds may be used in the development of assays and models for further enhancement of the understanding of the roles that inhibition of serine/threonine or tyrosine protein kinase (e.g., PKC, trk tyrosine kinase) play in the mechanistic aspects of the associated disorders and diseases. Thus, the compounds of the present invention are useful as diagnostic reagents in diagnostic assays, such as the assays described herein.

The inhibition of enzymatic activity by the isomeric fused pyrrolocarbazole and isoindolone compounds of the present invention can be determined using, for example, the following assays:
1. Vascular Endothelial Growth Factor Receptor (VEGFR) kinase inhibition assay;
2. trk A Tyrosine Kinase Activity inhibition assay;
3. PKC activity inhibition assay; and
4. Platelet Derived Growth Factor Receptor (PDGFR) inhibition assay.

Descriptions of these assays follow, but results obtained therein are not to be construed as limiting the scope of the disclosure. For convenience, certain abbreviations are used to delineate the results which are defined in the body of the text. Others are defined as follows: "$\mu$g" for microgram, "mg" for milligram, "g" for gram, "$\mu$L" for microliter, "mL" for milliliter, "L" for liter, "nM" for nanomolar, "$\mu$M" for micromolar, "mM" for millimolar, "M" for molar and "nm" for nanometer, "BSA" for benzene sulfonic acid, "ATP" for adenosine triphosphate, and "EGTA" for 1,2-di(2-aminoethoxy)ethane-N,N,N',N'-tetraacetic acid.

Inhibition of trkA Tyrosine Kinase Activity

Selected isomeric fused pyrrolocarbazole and isoindolone compounds were tested for their ability to inhibit the kinase activity of baculovirus-expressed human trkA cytoplasmic domain using an ELISA-based assay as previously described (Angeles et al., Anal. Biochem. 236: 49–55, 1996). Briefly, the 96-well microtiter plate was coated with substrate solution (recombinant human phospholipase C-$\gamma$I/glutathione S-transferase fusion protein (Rotin et al., EMBO J., 11: 559–567, 1992). Inhibition studies were performed in 100 $\mu$l assay mixtures containing 50 mM Hepes, pH 7.4, 40 $\mu$M ATP, 10 mM MnCl$_2$, 0.1% BSA, 2% DMSO, and various concentrations of inhibitor. The reaction was initiated by addition of trkA kinase and allowed to proceed for 15 minutes at 37° C. An antibody to phosphotyrosine (UBI) was then added, followed by a secondary enzyme-conjugated antibody, alkaline phosphatase-labelled goat anti-mouse IgG (Bio-Rad). The activity of the bound enzyme was measured via an amplified detection system (Gibco-BRL). Inhibition data were analyzed using the sigmoidal dose-response (variable slope) equation in GraphPad Prism. The concentration that resulted in 50% inhibition of kinase activity is referred to as "IC$_{50}$". The results are summarized in Table 5.

TABLE 5

Inhibitory Effects of Isomeric Fused Pyrrolocarbazoles and Isoindolones on trkA Kinase Activity

| Compound Number | trkA (% inhibition @ 300 nM) IC$_{50}$, nM |
|---|---|
| IV-1 | (0) |
| IV-2 | (2) |
| IV-3 | (18) |
| IV-4 | (23) |
| IV-5 | (14) |
| IV-6 | 0 |
| IV-7 | (7) |
| IV-8 | (4) |
| IV-9 | (6) |
| IV-10 | (6) |
| IV-11 | (4) |
| III-1 | (1) |
| III-2 | (5) |
| XIII | 0 |
| XVII | (10) |
| IX-1 | (9) |
| IX-2 | (9) |
| IX-3 | (25) |
| X-1 | (38) |
| X-2 | (30) |
| X-3 | (15) |
| X-4 | (15) |

Inhibition of Vascular Endothelial Growth Factor Receptor Kinase Activity

Isomeric fused pyrrolocarbazole and isoindolone compounds were examined for their inhibitory effects on the kinase activity of baculovirus-expressed VEGF receptor (human flk-1, KDR, VEGFR2) kinase domain using the procedure described for the trkA kinase ELISA assay described above. The kinase reaction mixture, consisting of 50 mM Hepes, pH 7.4, 40 $\mu$M ATP, 10 mM MnCl$_2$, 0.1% BSA, 2% DMSO, and various concentrations of inhibitor, was transferred to PLC-$\gamma$/GST-coated plates. VEGFR kinase was added and the reaction was allowed to proceed for 15 min at 37° C. Detection of phosphorylated product was accomplished by addition of anti-phosphotyrosine antibody (UBI). A secondary enzyme-conjugated antibody was delivered to capture the antibody-phosphorylated PLC-$\gamma$/GST complex The activity of the bound enzyme was measured via an amplified detection system (Gibco-BRL). Inhibition data were analyzed using the sigmoidal dose-response (variable slope) equation in GraphPad Prism. Results are summarized in Table 6.

TABLE 6

Inhibitory Effects of Isomeric Fused Pyrrolocarbazoles and Isoindolones on VEGF Receptor Kinase Activity

| Compound Number | VEGFR kinase (% inhibition @ 300 nM) IC$_{50}$, nM |
|---|---|
| IV-1 | 71 |
| IV-2 | 870 |
| IV-3 | 332 |
| IV-4 | (23) |
| IV-5 | 160 |
| IV-6 | (14) |
| IV-7 | 431 |
| IV-8 | (20) |
| IV-9 | 2863 |
| IV-10 | 5332 |
| IV-11 | 555 |
| IV-12 | (19) |
| IV-13 | (8) |
| IV-14 | (6) |
| IV-15 | (7) |
| IV-16 | (14) |
| IV-17 | (3) |
| IV-18 | (8) |
| IV-19 | (4) |
| IV-20 | (11) |
| IV-21 | (7) |
| IV-22 | (8) |
| IV-23 | (0) |
| IV-24 | (0) |
| IV-25 | (0) |
| IV-26 | (10) |
| IV-27 | (5) |
| IV-28 | (4) |
| IV-29 | (1) |
| IV-30 | (1) |
| IV-31 | (10) |
| IV-32 | (27) |
| IV-33 | (22) |
| IV-34 | (54) |
| IV-35 | (43); 316 |
| IV-36 | (17) |
| IV-37 | (11) |
| IV-38 | (5) |
| IV-39 | (8) |
| IV-40 | (10) |
| IV-41 | (34) |
| IV-42 | (42) |
| IV-43 | (8) |
| IV-44 | (3) |
| III-2 | (31) |
| XIII | 8391 |
| XVII | 796 |
| IX-1 | (10) |
| IX-2 | 8751 |
| IX-3 | (5) |
| IX-4 | (21) |
| IX-5 | (25) |
| IX-6/X-7 | (86) |
| X-1 | 166 |
| X-2 | 116 |
| X-3 | 1477 |
| X-4 | 138 |
| X-5 | (16) |
| X-6 | (40) |

Inhibition of Platelet Derived Growth Factor Receptor Kinase Activity

Isomeric fused pyrrolocarbazole and isoindolone compounds were examined for their inhibitory effects on the kinase activity of baculovirus-expressed PDGFP receptor kinase domain using the trkA kinase ELISA described above. Assays were performed in substrate PLC-γ/GST)-coated 96-well microtiter plates. Each 100-μl reaction mixture contained 50 mM HEPES, pH 7.4, 20 μM ATP, 10 mM MnCl$_2$, 0.1% BSA, 2% DMSO, and various concentrations of inhibitor. The reaction was initiated by addition of prephosphorylated recombinant human enzyme (10 ng/ml PDGFRβ) and allowed to proceed for 15 minutes at 3 7° C. The prephosphorylated enzyme was prepared prior to use by incubation of the kinase in buffer containing 20 μM ATP and 10 mM MnCl$_2$ for 1 hour at 4 C. Detection of phosphorylated product was done by adding horseradish peroxidase (HRP)-conjugated anti-phosphotyrosine antibody (UBI). The HRP substrate solution containing 3,3'-5,5'-tetramethylbenzidine and hydrogen peroxide was later added and the plates were incubated for 10 minutes at room temperature. The reaction was quenched with acid and the resulting absorbance was read at 450 nm using a Microplate Bio-kinetics Reader (Bio-Tek Instrument EL 312e). Inhibition data were analyzed using the sigmoidal dose-response (variable slope) equation in GraphPad Prism. The results are summarized in Table 7.

TABLE 7

PDGFRβ Inhibitory Effects of Isomeric Fused Pyrrolocarbazoles and Isoindolones

| Compound Number | PDGFRβ (% inhibition @ 1 μM) IC$_{50}$, nM |
|---|---|
| IV-1 | (6) |
| IV-2 | (17) |
| IV-3 | (0) |
| IV-4 | (0) |
| IV-5 | (26) |
| IV-7 | (15) |
| IV-9 | (20) |
| IV-10 | (11) |
| IV-11 | (6) |
| III-1 | (44) |
| III-2 | (9) |
| XIII | (10) |
| XVII | (24) |
| IX-1 | (23) |
| IX-2 | (8) |
| IX-3 | (16) |
| X-1 | (19) |
| X-2 | (16) |
| X-3 | (1) |

Dosage and Formulation

For therapeutic purposes, the compounds of the present invention can be administered by any means that results in the contact of the active agent with the agents site of action in the body of a mammal. The compounds may be administered by any conventional means available for use in conjunction with pharmaceuticals, either as individual therapeutic agents or in a combination of therapeutic agents. They are preferably administered as the sole active agent in a pharmaceutical composition, but alternatively, they can be used in combination with other active ingredients, e.g., other growth factors which facilitate neuronal survival or axonal regeneration in diseases or disorders. The compounds are preferably combined with a pharmaceutical carrier selected on the basis of the chosen route of administration and standard pharmaceutical practice.

The compounds can be formulated into pharmaceutical compositions, for example, by admixture with pharmaceutically acceptable nontoxic excipients and carriers. Such compositions can be prepared for use in parenteral administration, particularly in the form of liquid solutions or suspensions; or oral administration, particularly in the form of tablets or capsules; or intranasally, particularly in the form of powders, nasal drops, or aerosols; or dermally, via, for example, trans-dermal patches.

The composition can be conveniently administered in unit dosage form and may be prepared by any of the methods well known in the pharmaceutical art, for example, as described in *Remington's Pharmaceutical Sciences* (Mack Pub. Co., Easton, Pa., 1980). Formulations for parenteral administration may contain as common excipients sterile water or saline, polyalkylene glycols such as polyethylene glycol, oils and vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds.

Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for trans-dermal patches are preferably lipophilic emulsions.

Compounds of Formula I and pharmaceutically acceptable salts thereof can be administered orally or non-orally, e.g., as an ointment or an injection. The concentrations of the compounds of this invention in a therapeutic composition can vary. The concentration will depend upon factors such as the total dosage of the drug to be administered, the chemical characteristics (e.g., hydrophobicity) of the compounds employed, the route of administration, the age, body weight and symptoms of a patient, etc. The compounds of this invention may be provided in an aqueous physiological buffer solution containing about 0.1 to 10% w/v compound for parenteral administration. Typical dose ranges are from about 1 mg to about 1 μg/kg of body weight per day; a preferred dose range is from about 0.01 mg/kg to 100 mg/kg of body weight per day, and preferably about 0.1 to 20 mg/kg once to four times per day. A preferred dosage of drug to be administered is likely to depend on variables such as the type and extent of progression of the disease or disorder, the overall health status of the particular patient, the relative biological efficacy of the compound selected, and formulation of the compound excipient, and its route of administration.

The pharmaceutical compositions in accordance with the present invention can be prepared by uniformly mixing an effective amount of a compound of Formula I or a pharmaceutically acceptable salt thereof, as an active ingredient, with a pharmaceutically acceptable carrier. The carrier may take a wide range of forms according to the forms of composition suitable for administration. It is desired that such pharmaceutical compositions are prepared in a unit dose form suitable for oral or non-oral administration. The forms for non-oral administration include ointment and injection.

Tablets can be prepared using excipients such as lactose, glucose, sucrose, mannitol and methyl cellulose, disintegrating agents such as starch, sodium alginate, calcium carboxymethyl cellulose and crystalline cellulose, lubricants such as magnesium stearate and talc, binders such as gelatin, polyvinyl alcohol, polyvinyl pyrrolidone, hydroxypropyl cellulose and methyl cellulose, surfactants such as sucrose fatty acid ester and sorbitol fatty acid ester, and the like in a conventional manner. It is preferred that each tablet contains 15–300 mg of the active ingredient.

Granules can be prepared using excipients such as lactose and sucrose, disintegrating agents such as starch, binders such as gelatin, and the like in a conventional manner. Powders can be prepared using excipients such as lactose and mannitol, and the like in a conventional manner. Capsules can be prepared using gelatin, water, sucrose, gum arabic, sorbitol, glycerin, crystalline cellulose, magnesium stearate, talc, and the like in a conventional manner. It is preferred that each capsule contains 15–300 mg of the active ingredient.

Syrup preparations can be prepared using sugars such as sucrose, water, ethanol, and the like in a conventional manner.

Ointment can be prepared using ointment bases such as vaseline, liquid paraffin, lanolin and macrogol, emulsifiers such as sodium lauryl lactate, benzalkonium chloride, sorbitan mono-fatty acid ester, sodium carboxymethyl cellulose and gum arabic, and the like in a conventional manner.

Injectable preparations can be prepared using solvents such as water, physiological saline, vegetable oils (e.g., olive oil and peanut oil), ethyl oleate and propylene glycol, solubilizing agents such as sodium benzoate, sodium salicylate and urethane, isotonicity agents such as sodium chloride and glucose, preservatives such as phenol, cresol, p-hydroxybenzoic ester and chlorobutanol, antioxidants such as ascorbic acid and sodium pyrosulfite, and the like in a conventional manner.

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

What is claimed is:

1. A compound of Formula I:

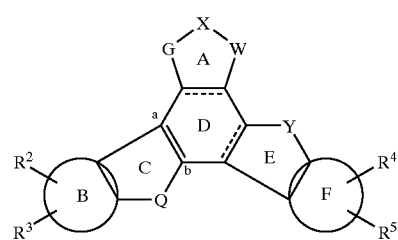

or a stereoisomer or pharmaceutically acceptable salt form thereof, wherein:

ring D is selected from phenyl and cyclohexene with double bond a-b;

ring B and ring F, independently, and each together with the carbon atoms to which they are attached, are selected from a 6-membered carbocyclic ring;

G—X—W is selected from:
  a) —(A$^1$A$^2$)C—N(R$^1$)—C(B$^1$B$^2$)—;
  b) —CH(R$^{1A}$)—C(=O)—N(R$^1$)—; and
  c) —N(R$^1$)—C(=O)—CH(R$^{1A}$)—;

R$^1$ is selected from:
  a) H, substituted or unsubstituted alkyl of 1 to 6 carbons, substituted or unsubstituted aryl, substituted or unsubstituted arylalkyl, substituted or unsubstituted heteroaryl, or substituted or unsubstituted heteroarylalkyl;
b) —C(=O)R$^7$, where R$^7$ is selected from substituted or unsubstituted alkyl, substituted or unsubstituted aryl, substituted or unsubstituted carbocyclic group, and substituted or unsubstituted heterocyclyl groups;
c) —OR$^8$, where R$^8$ is selected From H and alkyl having from 1 to 6 carbons;
d) —C(=O)NHR$^8$, —NR$^9$R$^{10}$, —(CH$_2$)$_p$NR$^9$R$^{10}$, —(CH$_2$)$_p$OR$^8$, —O(CH$_2$)$_p$OR$^8$ and —O(CH$_2$)$_p$NR$^9$R$^{10}$, where p is from 1 to 4; and where either
1) R$^9$ and R$^{10}$ are each independently selected from H, unsubstituted alkyl of 1 to 6 carbons, and substituted alkyl; or
2) R$^9$ and R$^{10}$ together form a linking group of the formula —(CH$_2$)$_2$—X$^1$—(CH$_2$)$_2$—, wherein X$^1$ is selected from —O—, —S—, and —CH$_2$—;
R$^{1A}$ is the same as R$^1$;
R$^2$, R$^3$, R$^4$ and R$^5$ are each independently selected from:
a) H, aryl, carbocyclyl, heterocyclyl, —CN, CF$_3$, —NO$_2$, —OH, —OR$^7$, Br, I, —O(CH$_2$)$_p$NR$^9$R$^{10}$, —OC(=O)R$^7$, —OC(=O)NR$^9$R$^{10}$, —O(CH$_2$)$_p$OR$^8$, F, Cl, —CH$_2$OR$^8$, —NR$^9$R$^{10}$, —NR$^8$S(=O)$_2$R$^7$, —NR$^8$C(=O)R$^7$, or —NR$^8$C(=S)R$^7$;
b) —CH$_2$OR$^{11}$, where R$^{11}$ is the residue of an amino acid after the hydroxyl group of the carboxyl group is removed;
c) —NR$^8$C(=O)NR$^9$R$^{10}$, —NR$^8$C(=S)NR$^9$R$^{10}$, —CO$_2$R$^{12}$, —C(=O)R$^{12}$, —C(=O)NR$^9$R$^{10}$, —C(=S)NR$^9$R$^{10}$, —CH=NOR$^{12}$, —CH=NR$^7$, —(CH$_2$)$_p$NR$^9$R$^{10}$, —(CH$_2$)$_p$NHR$^{11}$, or —CH=NNR$^{12}$R$^{12A}$; where
R$^{12}$ is selected from H, alkyl of 1 to 6 carbons, —OH, alkoxy of 1 to 6 carbons, —OC(=O)R$^7$, —OC(=O)NR$^9$R$^{10}$, —OC(=S)NR$^9$R$^{10}$, —O(CH$_2$)$_p$NR$^9$R$^{10}$, —O(CH$_2$)$_p$OR$^8$, substituted or unsubstituted arylalkyl having from 6 to 10 carbons, substituted or unsubstituted heterocyclylalkyl, and a substituted or unsubstituted carbocyclic group;
R$^{12A}$ is the same R$^{12}$;
d) —S(O)$_y$R$^{12}$, —(CH$_2$)$_p$S(O)$_y$R$^7$, —CH$_2$S(O)$_y$R$^{11}$ where y is 0, 1 or 2;
e) alkyl of 1 to 8 carbons, alkenyl of 2 to 8 carbons, and alkynyl of 2 to 8 carbons, wherein:
1) each alkyl, alkenyl, or alkynyl group is unsubstituted; or
2) each alkyl, alkenyl or alkynyl group is substituted with 1 to 3 groups selected from aryl of 6 to 10 carbons, heterocyclyl, arylalkoxy, heterocycloalkoxy, hydroxylalkoxy, alkytoxyalkoxy, hydroxyalkylthio, alkoxy-alkylthio, F, Cl, Br, I, —CN, —NO$_2$, —OH, —OR$^7$, —X$^2$CH$_2$)$_p$C(=O)NR$^9$R$^{10}$, —X$^2$(CH$_2$)—C(=S)NR$^9$R$^{10}$, —X$^2$(CH$_2$)$_p$OC(=O)NR$^9$R$^{10}$, —X$^2$(CH$_2$)$_p$CO$_2$R$^7$, —X$^2$(CH$_2$)$_p$S(O)$_y$R$^7$, —X$^2$(CH$_2$)$_p$NR$^8$C(=O)NR$^9$R$^{10}$, —OC(=O)R$^7$, —OC(=O)NHR$^{12}$, O-tetrahydropyranyl, —NR$^9$R$^{10}$, —NR$^8$CO$_2$R$^7$, 13 NR$^8$C(=O)NR$^9$R$^{10}$, —NR$^8$C(=S)NR$^9$R$^{10}$, —NHC(=NH)NH$_2$, —NR$^8$C(=O)R$^7$, —NR$^8$C(=S)R$^7$, —NR$^8$S(=O)$_2$R$^7$, —S(O)$_y$R$^7$, —CO$_2$R$^{12}$, —C(=O)NR$^9$R$^{10}$, —C(=S)NR$^9$R$^{10}$, —C(=O)R$^{12}$, —CH$_2$OR$^8$, —CH=NNR$^{12}$R$^{12a}$, —CH=NOR$^{12}$, —CH=NR$^7$, —CH=NNHCH(N=NH)NH$_2$, —S(=O)$_2$NR$^{12}$R$^{12A}$, —P(=O)(OR$^8$)$_2$, and —OR$^{11}$, and a monosaccharide of 5 to 7 carbons where each hydroxyl group of the monosaccharide is independently either unsubstituted or is replaced by H, alkyl of 1 to 4 carbons, alkylcarbonyloxy of 2 to 5 carbons, or alkoxy of 1 to 4 carbons;
X$^2$is O, S, or NR$^8$;
Q is selected from —NR$^6$;
R$^6$ is selected from —H, —SO$_2$R$^7$, —CO$_2$R$^7$, —CO(=O)R$^7$, —C(=O)NR$^9$R$^{10}$, alkyl of 1–8 carbons, alkenyl of 2–8 carbons, and alkynyl of 2–8 carbons; and either
1) each alkyl, alkenyl, or alkynyl group is unsubstituted; or
2) each alkyl, alkenyl, or alkynyl group independently is substituted, as defined for R$^2$, R$^3$, R$^4$, and R$^5$ in e) above;
Y is selected from:
a) an unsubstituted alkylene of 2 carbons;
b) an alkylene of 2 carbons substituted with R$^{13}$, where R$^{13}$ is selected from R$^2$thioalkyl of 1–4 carbons, halogen, alkyl of 1–8 carbons, alkenyl of 2–8 carbons, and alkynyl of 2–8 carbons, where
i) each alkyl of 1–8 carbons, alkenyl of 2–8 carbons, and alkynyl of 2–8 carbons is unsubstituted; or
ii) each alkyl of 1–8 carbons, alkenyl of 2–8 carbons, and alkynyl of 2–8 carbons, independently, is substituted, as defined for R$^2$, R$^3$, R$^4$, and R$^5$ in e) above; and
c) a functional group selected from —CH=CH—, —CH(OH)—CH(OH)—, —C=C(R$^{13}$)$_2$—, —C(=O)CH(R$^6$)—, —CH(R$^6$)C(=O)—, —C(=NOR$^{12}$)CH(R$^6$)—, —CHR$^8$C(=NOR$^{12}$)—, —CH$_2$Z—, —ZCH$_2$—, where Z is selected from —C(R$^{12}$)—;
A$^1$ and A$^2$ are selected from H, H; H, OR$^{12}$; H, —SR$^{12}$; H, —N(R$^{12}$)$_2$; and a group where A$^1$ and A$^2$ together form a moiety selected from =O, =S, and =NR$^{12}$; and,
B$^1$ and B$^2$ are selected from H, H; H, —OR$^{12}$; H, —SR$^{12}$; H, —N(R$^{12}$)$_2$; and a group where B$^1$ and B$^2$ together form a moiety selected from =O, =S, and =NR$^{12}$; with the proviso that at least one of the pairs A$^1$ and A$^2$, or B$^1$ and B$^2$, form =O.

2. The compound of claim 1 wherein R$^1$, R$^3$, and R$^5$ are H.

3. The compound of claim 2 wherein —G—X—W— is —CH$_2$N(R$^1$)C(=O)—, —C(=O)N(R$^1$)CH$_2$—, or —C(=O)N(R$^1$)C(=O)—.

4. The compound of claim 1 wherein rings B and F are independently substituted or unsubstituted phenyl.

5. The compound of claim 1 wherein Q is —NR$^6$, and R$^6$ is H or substituted or unsubstituted lower alkyl.

6. The compound of claim 1 wherein Y is an unsubstituted alkylene of 2 carbons or —CH=CH—.

7. The compound of claim 1 having formula:

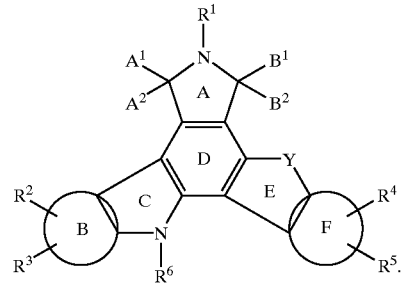

8. The compound of claim 7 wherein rings B and F are phenyl.

9. The compound of claim 8 wherein $R^1$, $R^3$, and $R^5$ are H.

10. The compound of claim 8 wherein $A^1$ and $A^2$ are selected from H, H; H, OH; H, —OCH$_3$; H, —N(R$^{12}$)$_2$; or a group where $A^1$ and $A^2$ together form =O or =NR$^{12}$; $B^1$ and $B^2$ are selected from H, H; H, OH; H, —OCH$_3$; H, —N(R$^{12}$)$_2$; or a group where $B^1$ and $B^2$ together form =O or =NR$^{12}$; and $R^{12}$ is H, methyl, ethyl, propyl, —OH, or methoxy.

11. The compound of claim 8 wherein $R^6$ is H or substituted or unsubstituted lower alkyl.

12. The compound of claim 7, wherein Y is an unsubstituted alkylene of 2 carbons or —CH=CH—.

13. The compound of claim 1 having the formula:

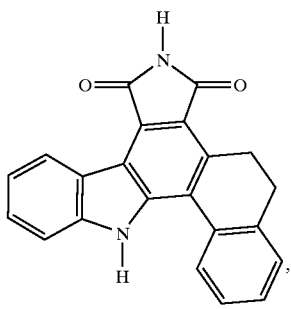

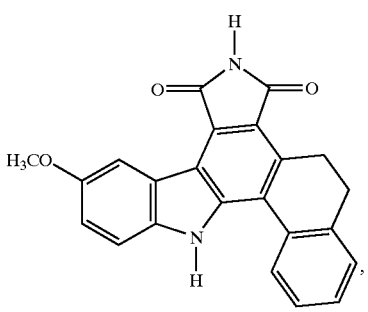

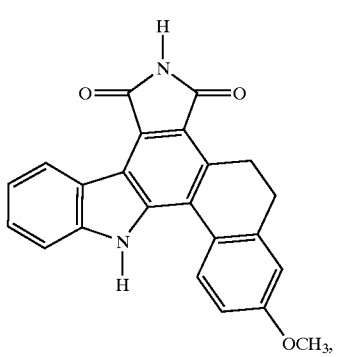

-continued

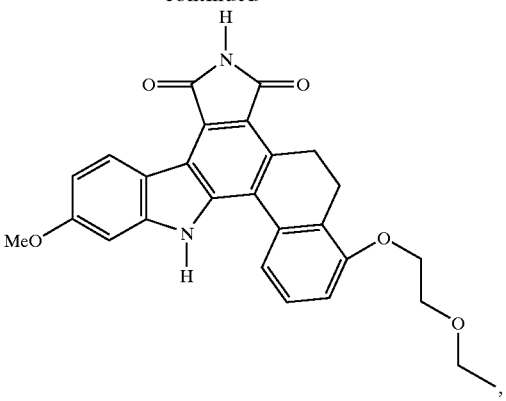

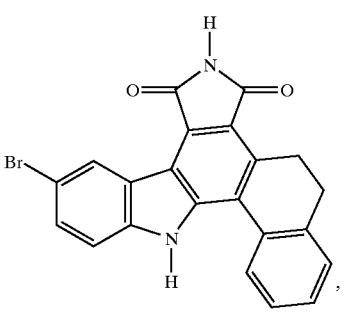

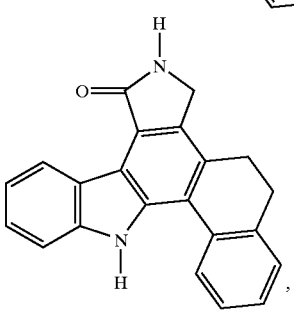

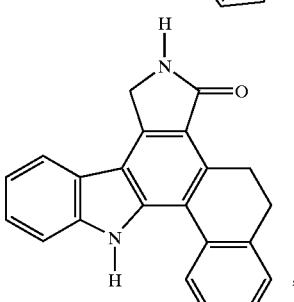

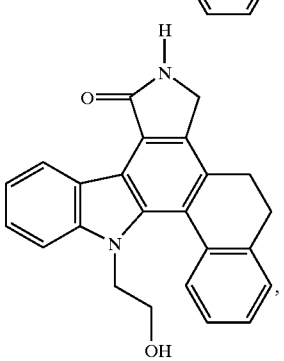

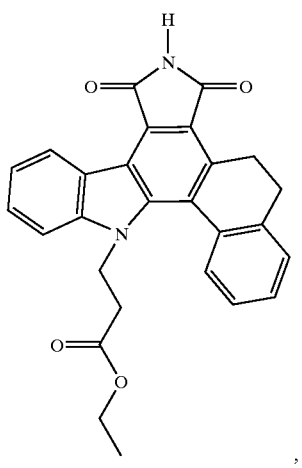
,
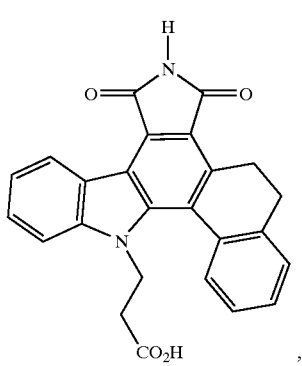
,
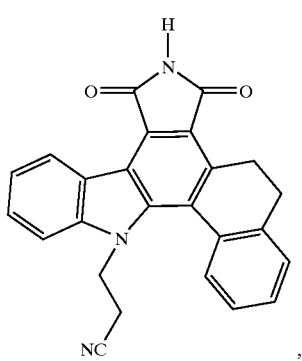
,
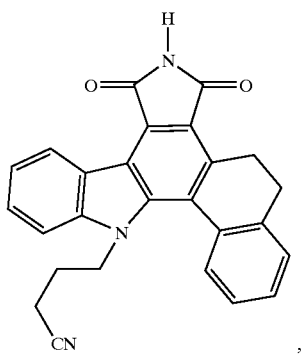
,
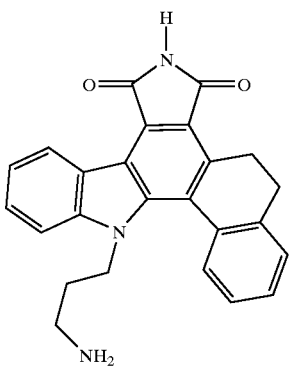
,
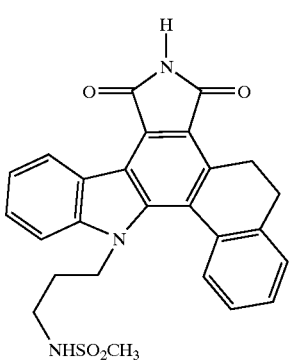
,
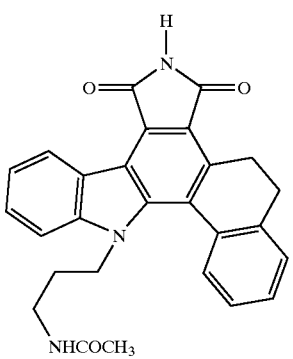
,
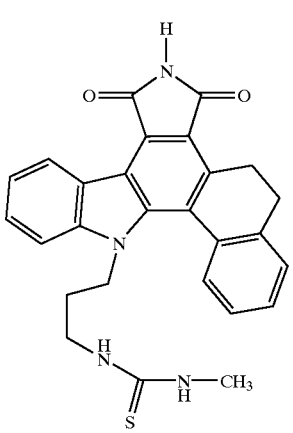
,

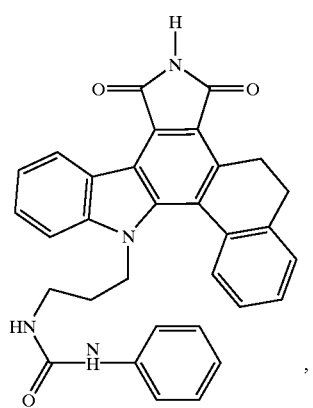
,
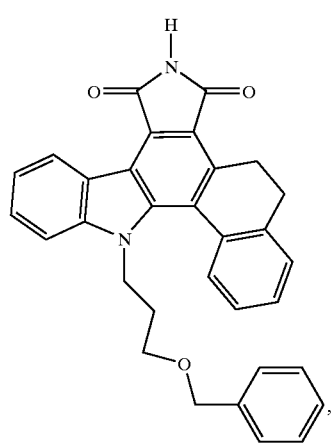
,
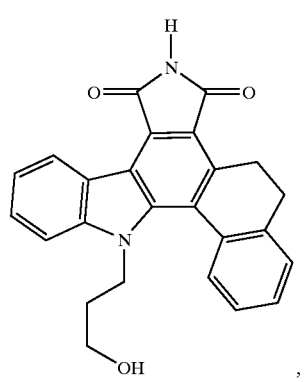
,
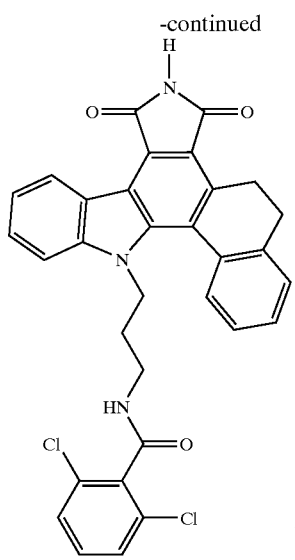
,
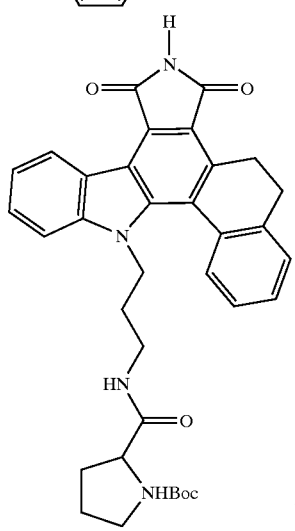
,
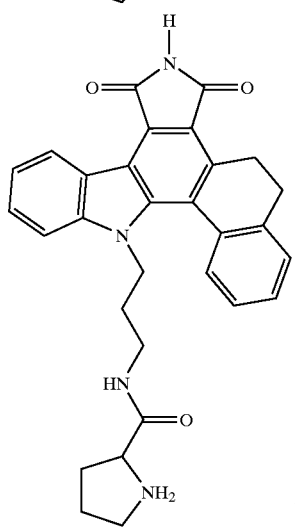
,

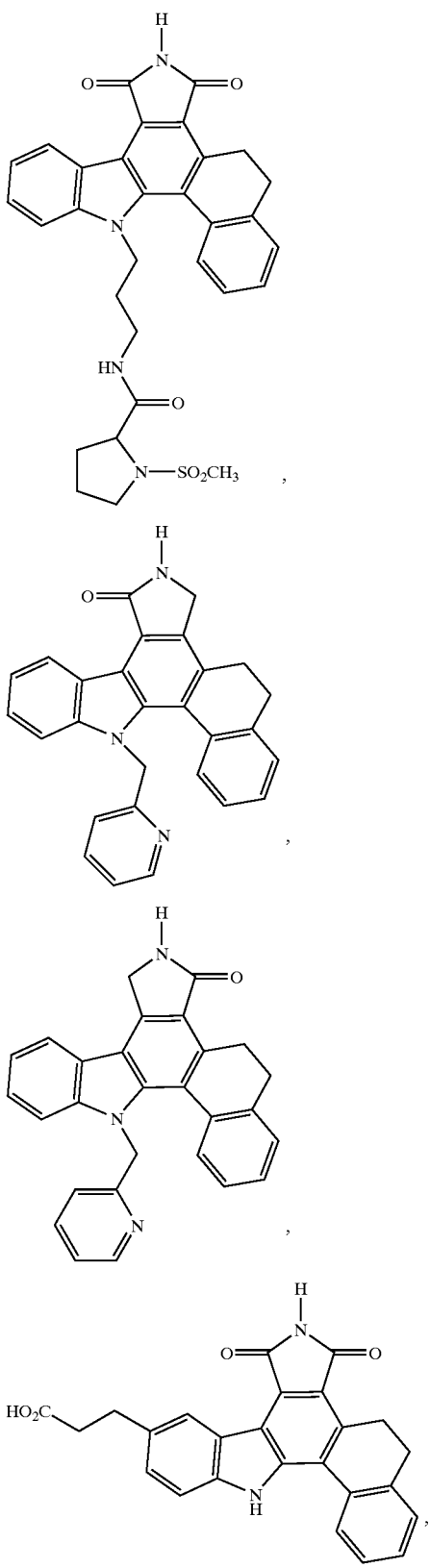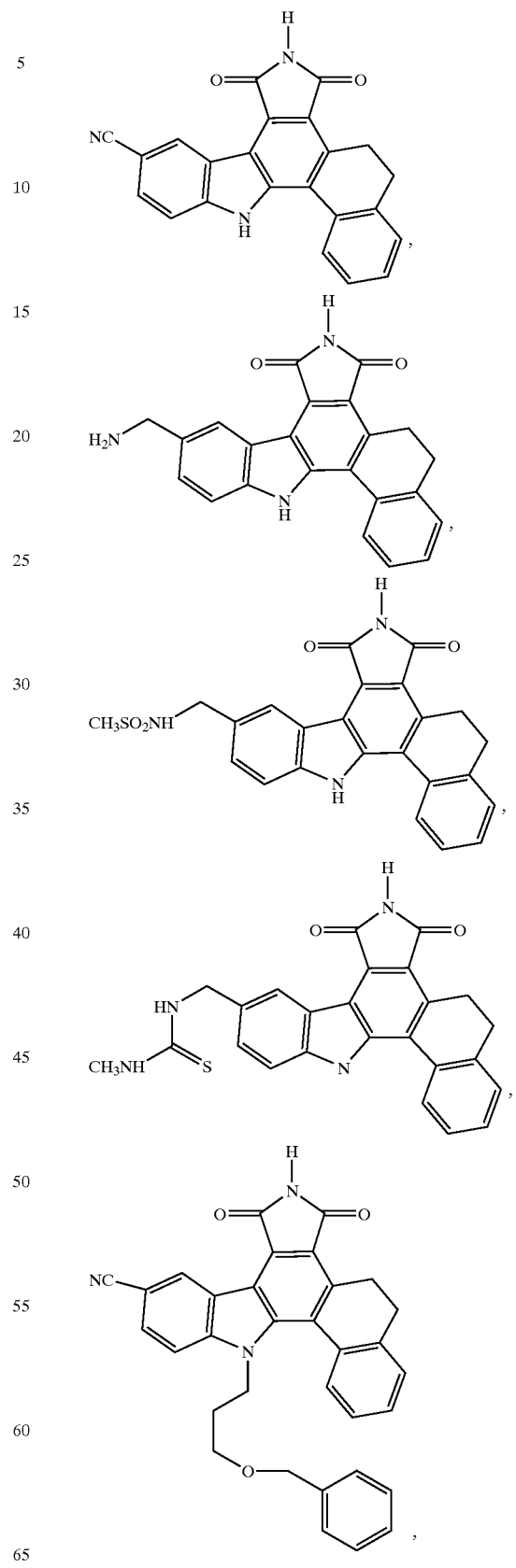

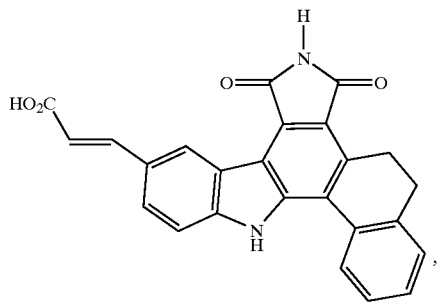
,
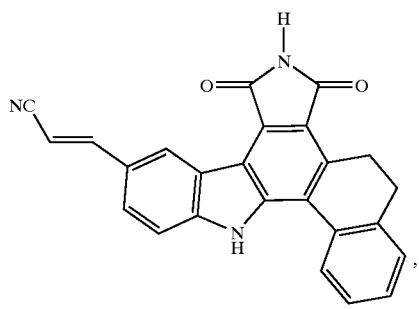
,
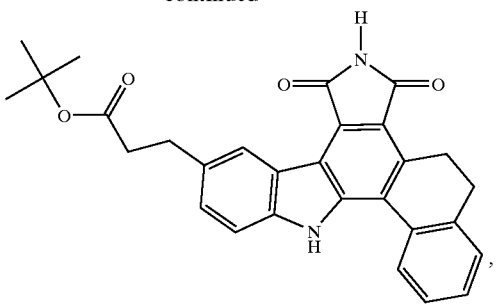
or
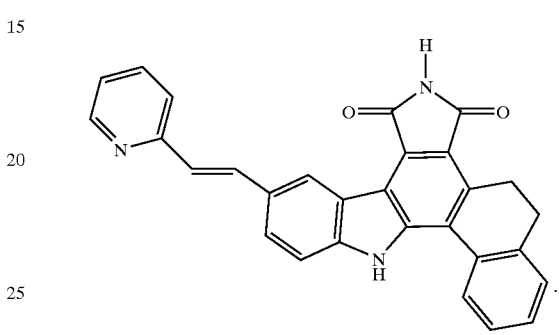
.
14. A pharmaceutical composition comprising a compound of claim 1 and a pharmaceutically acceptable carrier.
15. A pharmaceutical composition comprising a compound of claim 13 and a pharmaceutically acceptable carrier.
* * * * *